United States Patent
Dayton et al.

(10) Patent No.: US 10,493,038 B2
(45) Date of Patent: *Dec. 3, 2019

(54) FORMULATION OF ACOUSTICALLY ACTIVATABLE PARTICLES HAVING LOW VAPORIZATION ENERGY AND METHODS FOR USING SAME

(71) Applicants: The University of North Carolina at Chapel Hill, Chapel Hill, NC (US); The Arizona Board of Regents on behalf of The University of Arizona, Tucson, AZ (US); The Regents of the University of Colorado, a body corporate, Denver, CO (US)

(72) Inventors: Paul Alexander Dayton, Carrboro, NC (US); Paul Steven Sheeran, Durham, NC (US); Terry Onichi Matsunaga, Tucson, AZ (US); Mark A. Borden, Boulder, CO (US)

(73) Assignees: The University of North Carolina at Chapel Hill, Chapel Hill, NC (US); The Arizona Board of Regents on Behalf of the University of Arizona, Tucson, AZ (US); The Regents of the University of Colorado, Denver, CO (US)

(*) Notice: Subject to any disclaimer, the term of this patent is extended or adjusted under 35 U.S.C. 154(b) by 0 days.

This patent is subject to a terminal disclaimer.

(21) Appl. No.: 15/880,481

(22) Filed: Jan. 25, 2018

(65) Prior Publication Data

US 2018/0221515 A1    Aug. 9, 2018

Related U.S. Application Data

(62) Division of application No. 15/247,840, filed on Aug. 25, 2016, which is a division of application No. 13/876,165, filed as application No. PCT/US2011/055713 on Oct. 11, 2011, now Pat. No. 9,427,410.

(60) Provisional application No. 61/391,569, filed on Oct. 8, 2010, provisional application No. 61/505,915, filed on Jul. 8, 2011.

(51) Int. Cl.
| | |
|---|---|
| A61K 9/51 | (2006.01) |
| A61K 49/22 | (2006.01) |
| A61K 41/00 | (2006.01) |
| B01J 13/02 | (2006.01) |
| A61K 49/00 | (2006.01) |
| A61K 47/06 | (2006.01) |
| A61K 48/00 | (2006.01) |

(52) U.S. Cl.
CPC .............. *A61K 9/51* (2013.01); *A61K 9/5123* (2013.01); *A61K 9/5192* (2013.01); *A61K 41/0028* (2013.01); *A61K 47/06* (2013.01); *A61K 49/0002* (2013.01); *A61K 49/221* (2013.01); *A61K 49/223* (2013.01); *A61K 49/226* (2013.01); *B01J 13/02* (2013.01); *A61K 48/00* (2013.01)

(58) Field of Classification Search
None
See application file for complete search history.

(56) References Cited

U.S. PATENT DOCUMENTS

| | | | |
|---|---|---|---|
| 4,957,656 A | 9/1990 | Cerny et al. | |
| 5,469,854 A | 11/1995 | Unger | |
| 5,558,853 A | 9/1996 | Quay | |
| 5,585,112 A | 12/1996 | Unger et al. | |
| 5,716,597 A | 2/1998 | Lohrmann et al. | |
| 5,730,955 A | 3/1998 | Lohrmann | |
| 5,740,596 A | 4/1998 | Corl et al. | |
| 5,840,276 A | 11/1998 | Apfel | |
| 5,879,303 A | 3/1999 | Averkiou et al. | |
| 5,906,580 A | 5/1999 | Kline-Schoder et al. | |

(Continued)

FOREIGN PATENT DOCUMENTS

| | | |
|---|---|---|
| CA | 2 773 181 | 2/2018 |
| EP | 1 073 716 B1 | 4/2004 |

(Continued)

OTHER PUBLICATIONS

Seo et al. Microfluidic consecutive flow-focusing droplet generators. 2007 Soft Matter 3: 986-992. (Year: 2007).*
Non-Final Office Action for U.S. Appl. No. 15/035,211 (dated Feb. 9, 2018).
Wu, "Sonograpic Demonstration of Duodenobiliary Reflux with Soda Enhancement," Journal of Clinical Ultrasound, vol. 32, No. 5, pp. 249-252 (Nov. 10, 2003).
Doinikov et al., "Review of shell models for contrast agent microbubbles," IEEE Trans. Ultrason. Ferroelectr. Freq. Control, vol. 58, pp. 981-993 (2011).

(Continued)

*Primary Examiner* — Jennifer A. Lamberski
(74) *Attorney, Agent, or Firm* — Jenkins, Wilson, Taylor & Hunt, P.A.

(57) ABSTRACT

An acoustically activatable particle of material includes a first substance that includes a component that is a gas 25° C. and atmospheric pressure. A second substance, different from the first substance, encapsulates the first substance to create a droplet or emulsion that is stable at room temperature and atmospheric pressure. At least some of the first substance exists in a gaseous phase at the time of encapsulation of the first substance within the second substance to form a bubble. After formation of the bubble, the bubble is condensed into a liquid phase, which causes the bubble to transform into the droplet or emulsion having a core consisting of a liquid. The droplet or emulsion is an activatable phase change agent having a core consisting of a liquid at 25° C. and atmospheric pressure. The first substance has a boiling point below 25° C. at atmospheric pressure.

14 Claims, 9 Drawing Sheets

(56) References Cited

U.S. PATENT DOCUMENTS

Figure 1:
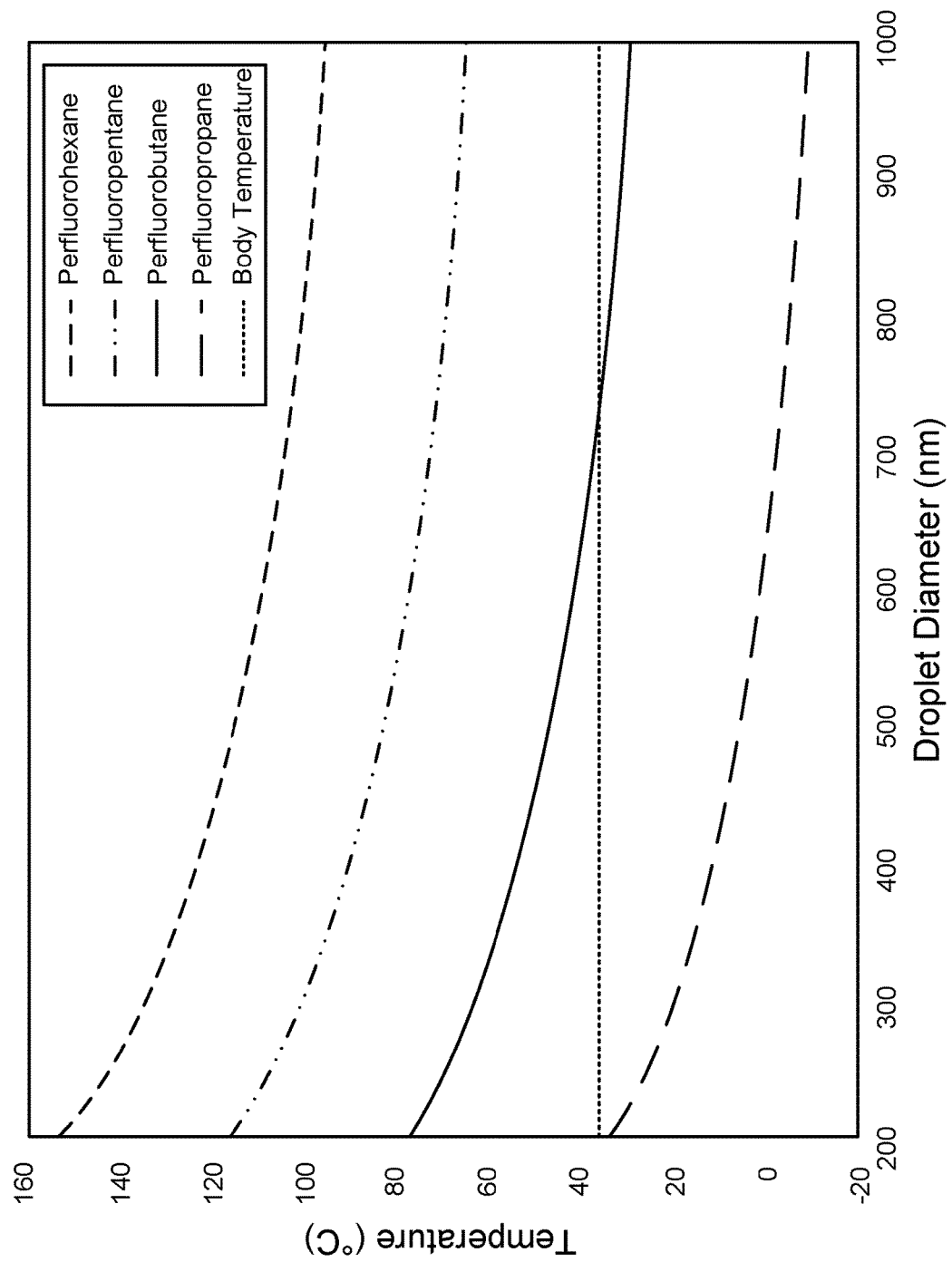

| | | | |
|---|---|---|---|
| 6,033,645 | A | 3/2000 | Unger et al. |
| 6,071,495 | A | 6/2000 | Unger et al. |
| 6,312,383 | B1 | 11/2001 | Lizzi et al. |
| 6,371,917 | B1 | 4/2002 | Ferrara et al. |
| 6,409,667 | B1 | 6/2002 | Hossack |
| 6,740,039 | B1 | 5/2004 | Rafter et al. |
| 7,358,226 | B2 | 4/2008 | Dayton et al. |
| 9,427,410 | B2 | 8/2016 | Dayton et al. |
| 9,532,769 | B2 | 1/2017 | Dayton et al. |
| 9,982,290 | B2 | 5/2018 | Janzen et al. |
| 2001/0019710 | A1 | 9/2001 | Berg et al. |
| 2001/0028893 | A1 | 11/2001 | Spears |
| 2003/0165431 | A1 | 9/2003 | Pines et al. |
| 2005/0038423 | A1 | 2/2005 | Inder et al. |
| 2005/0084538 | A1 | 4/2005 | Dayton et al. |
| 2006/0078501 | A1 | 4/2006 | Goertz et al. |
| 2007/0035204 | A1 | 2/2007 | Angelsen et al. |
| 2007/0292495 | A1 | 12/2007 | Ludwig et al. |
| 2008/0182237 | A1 | 7/2008 | Bentwich et al. |
| 2008/0311046 | A1 | 12/2008 | Kawabata et al. |
| 2009/0023597 | A1 | 1/2009 | Wong et al. |
| 2009/0076394 | A1 | 3/2009 | Wong et al. |
| 2009/0117177 | A1 | 5/2009 | Rapoport et al. |
| 2009/0182237 | A1 | 7/2009 | Bjorn et al. |
| 2009/0317884 | A1 | 12/2009 | Laugharn, Jr. |
| 2010/0009424 | A1 | 1/2010 | Forde et al. |
| 2011/0044903 | A1 | 2/2011 | Borrelli |
| 2012/0172720 | A1 | 7/2012 | Asami et al. |
| 2012/0220869 | A1 | 8/2012 | Dayton et al. |
| 2012/0270177 | A1 | 10/2012 | Nakashima et al. |
| 2013/0053691 | A1 | 2/2013 | Kawabata et al. |
| 2013/0336891 | A1 | 12/2013 | Dayton et al. |
| 2015/0252355 | A1 | 9/2015 | Janzen et al. |
| 2016/0262727 | A1 | 9/2016 | Dayton et al. |
| 2016/0361447 | A1 | 12/2016 | Dayton et al. |
| 2018/0274008 | A1 | 9/2018 | Janzen et al. |

FOREIGN PATENT DOCUMENTS

| | | |
|---|---|---|
| WO | WO 2011/029094 A2 | 3/2011 |
| WO | WO 2011/149985 A1 | 12/2011 |
| WO | WO 2014/055832 A1 | 4/2014 |
| WO | WO 2015/070186 A1 | 5/2015 |

OTHER PUBLICATIONS

King et al., "Comparison between maximum radial expansion of ultrasound contrat agents and experimental postexcitation signal results," J. Acoust. Soc. Am., vol. 129, pp. 114-121 (2011).
King et al., "Determination of postexcitation thresholds for single ultrasound contrast agent microbubbles using double passive cavitation detection," J. Acoust. Soc. Am., vol. 127, pp. 3449-3455 (2010).
Notice of Allowance and Fee(s) Due and Examiner Initiated Interview Summary for U.S. Appl. No. 14/432,747 (dated Jan. 10, 2018).
Applicant Initiated Interview Summary for U.S. Appl. No. 14/432,747 (dated Jul. 24, 2017).
Notice of Allowance for Canadian Patent Application No. 2,773,181 (dated Jul. 10, 2017).
Final Office Action for U.S. Appl. No. 14/432,747 (dated May 19, 2017).
Applicant-Initiated Interview Summary for U.S. Appl. No. 14/432,747 (dated Feb. 22, 2017).
Non-Final Office Action for U.S. Appl. No. 14/432,747 (dated Oct. 12, 2016).
Office Action for Canadian Patent Application No. 2,773,181 (dated Sep. 12, 2016).
Commonly-assigned, co-pending U.S. Appl. No. 15/247,842 for "Formulation of Acoustically Activatable Particles Having Low Vaporization Energy and Methods for Using Same," (Unpublished, filed Aug. 25, 2016).
Notice of Allowance and Fee(s) Due for U.S. Appl. No. 13/393,500 (dated Aug. 22, 2016).
Applicant-Initiated Interview Summary for U.S. Appl. No. 13/393,500 (dated Jun. 21, 2016).
Restriction/Election Requirement for U.S. Appl. No. 14/432,747 (dated Jun. 3, 2016).
Notice of Allowance, Examiner-Initiated Interview Summary, and AFCP 2.0 Decision for U.S. Appl. No. 13/876,165 (dated Apr. 28, 2016).
Applicant-Initiated Interview Summary for U.S. Appl. No. 13/876,165 (dated Mar. 28, 2016).
Final Office Action for U.S. Appl. No. 13/393,500 (dated Feb. 24, 2016).
Final Office Action for U.S. Appl. No. 13/876,165 (dated Dec. 31, 2015).
Applicant-Initiated Interview Summary for U.S. Appl. No. 13/393,500 (dated Nov. 16, 2015).
Non-Final Office Action for U.S. Appl. No. 13/393,500 (dated Jul. 9, 2015).
Non-Final Office Action for U.S. Appl. No. 13/876,165 (dated Jun. 10, 2015).
Notification of Transmittal of the International Search Report and the Written Opinion of the International Searching Authority, or the Declaration for PCT International Application No. PCT/US2014/064889 (dated Apr. 9, 2015).
Restriction and/or Election Requirement for U.S. Appl. No. 13/393,500 (dated Jan. 27, 2015).
Restriction and/or Election Requirement for U.S. Appl. No. 13/876,165 (dated Dec. 1, 2014).
Notification of Transmittal of the International Search Report and the Written Opinion of the International Searching Authority, or the Declaration for PCT International Application No. PCT/US2013/063397 (dated Jan. 16, 2014).
Notification of Transmittal of the International Search Report and the Written Opinion of the International Searching Authority, or the Declaration for PCT International Application No. PCT/US2011/055713 (dated May 18, 2012).
Notification of Transmittal of the International Search Report and the Written Opinion of the International Searching Authority, or the Declaration for PCT International Application No. PCT/US2010/047988 (dated Mar. 31, 2011).
Ainslie et al., "Review of scattering and extinction cross-sections, damping factors, and resonance frequencies of a spherical gas bubble," The Journal of the Acoustical Society of America, vol. 130, pp. 3184-3208 (2011).
Alexandridis et al., "Surface Activity of Poly(ethylene oxide)-block-Poly(propylene oxide)-block-Poly(ethylene oxide) Copolymers," Langmuir, vol. 10, pp. 2604-2612 (1994).
Allen et al., "Effect of Coupled Oscillations on Microbubble Behavior," The Journal of the Acoustical Society of America, vol. 14, No. 3, pp. 1678-1690 (Sep. 2003).
Allen, "Liposomes—Opportunities in Drug Delivery," Drugs, vol. 54, Suppl. 4, pp. 8-14 (1997).
Anderson et al., "Ultrasound Molecular Imaging of Tumor Angiogenesis with an Integrin Targeted Microbubble Contrast Agent," Invest Radiol, vol. 46, No. 4, pp. 1-21 (Apr. 2011).
Anderson, "Shotgun DNA Sequencing Using Cloned DNase I-generated Fragments," Nucleic Acids Research, vol. 9, No. 13, pp. 3015-3027 (Jul. 1981).
Aparicio et al., "Chromatin Immunoprecipitation for Determining the Association of Proteins with Specific Genomic Sequences in Vivo," Current Protocols in Cell Biology, Chapter 17, Unit 17.7, pp. 17.7.1-17.7.23 (2004).
Apfel, "Activatable infusable dispersions containing drops of a superheated liquid for methods of therapy and diagnosis," (1998).
Asami et al., "Acoustic Signal Characterization of Phase Change Nanodroplets in Tissue-Mimicking Phantom Gels," Jpn. J. Appl. Phys., vol. 49 (2010).
Asami et al., "Repeatable vaporization of optically vaporizable perfluorocarbon droplets for photoacoustic contrast enhanced imaging," 2012 IEEE International Ultrasonics Symposium (IUS), pp. 1200-1203 (2012).

(56) References Cited

OTHER PUBLICATIONS

Auton et al., "The Force Exerted on a Body in an Inviscid Unsteady Non-Uniform Rotational Flow," J. Fluid Mech., vol. 197, pp. 241-257 (1988).
Behm et al., "Cellular and Molecular Imaging with Targeted Contrast Ultrasound," Ultrasound Quarterly, vol. 22, No. 1, pp. 67-72 (Mar. 2006).
Bekeredjian et al., "Therapeutic Use of Ultrasound Targeted Microbubble Destruction: A Review of Non-Cardiac Applications," Ultraschall in Med, vol. 27, pp. 134-140 (2006).
Bekeredjian et al., "Ultrasound-targeted Microbubble Destruction Can Repeatedly Direct Highly Specific Plasmid Expression to the Heart," Circulation—Journal of the American Heart Association, vol. 108, pp. 1022-1026 (2003).
Bernasconi et al., "A Chemogenomic Analysis of the Human Proteome: Application to Enzyme Families," Journal of Biomolecular Screening, vol. 12, No. 7, pp. 972-982 (2007).
Bloch et al., "Targeted Imaging Using Ultrasound Contrast Agents," IEEE Engineering in Medicine and Biology, vol. 23, No. 5, pp. 18-29 (Sep./Oct. 2004).
Böhmer et al., "Preparation of Monodisperse Polymer Particles and Capsules by Ink-Jet Printing," Colloids and Surfaces A: Physicochem. Eng. Aspects, vol. 289, pp. 96-104 (2006).
Borden et al., "A Stimulus-Responsive Contrast Agent for Ultrasound Molecular Imaging," Biomaterials, vol. 29, No. 5, pp. 1-19 (Feb. 2008).
Borden et al., "Ultrasound Radiation Force Modulates Ligand Availability on Targeted Contrast Agents," Molecular Imaging, vol. 5, No. 3, pp. 139-147 (Jul. 2006).
Borden et al., "Influence of Lipid Shell Physicochemical Properties on Ultrasound-Induced Microbubble Destruction," IEEE Transactions on Ultrasonics, Ferroelectrics, and Frequency Control, vol. 52, No. 11, pp. 1992-2002 (Nov. 2005).
Borden et al., "Surface Phase Behavior and Microstructure of Lipid/PEG-Emulsifier Monolayer-Coated Microbubbles," Colloids and Surfaces B: Biointerfaces, vol. 35, pp. 209-223 (Mar. 2004).
Borden et al., "Dissolution Behavior of Lipid Monolayer-Coated, Air-Filled Microbubbles: Effect of Lipid Hydrophobic Chain Length," Langmuir, vol. 18, pp. 9225-9233 (2002).
Bouakaz et al., "Contrast Superharmonic Imaging: A Feasability Study," Ultrasound in Med. & Biol., vol. 29, No. 4, pp. 547-553 (2003).
Bouakaz et al., "Super Harmonic Imaging: A New Imaging Technique for Improved Contrast Detection," Ultrasound in Med.& Biol., vol. 28, No. 1, pp. 59-68 (2002).
Brennen, "Cavitation and Bubble Dynamics," Oxford University Press (1995).
Burger et al., "Sequencing Complete Mitochondrial and Plastid Genomes," Nature Protocols, vol. 2, No. 3, pp. 603-614 (Mar. 22, 2007).
Burns et al., "Microbubble Contrast for Radiological Imaging: 1. Principles," Ultrasound Quarterly, vol. 22, No. 1, pp. 5-13 (Mar. 2006).
Calderon et al., "A boundary element model of the ransport of a semi-infinite bubble through a microvessel birfurcation," Physics of Fluids, vol. 22, p. 11 (2010).
Campbell, "Tumor Physiology and Delivery of Nanopharmaceuticals," Anti-Cancer Agents in Medicinal Chemistry, vol. 6, No. 6, pp. 503-512 (2006).
Carson et al., "Acoustic Droplet Vaporization," http://www.ultrasound.med.umich.edu/Projects/ADV.html, pp. 1-4 (Downloaded from the Internet Mar. 17, 2015).
Caskey et al., "Direct Observations of Ultrasound Microbubble Contrast Agent Interaction with the Microvessel Wall," The Journal of the Acoustical Society of America, vol. 122, No. 2, pp. 1191-1200 (Aug. 2007).
Chatterjee et al., "A Newtonian Rheological Model for the Interface of Microbubble Contrast Agents," Ultrasound in Med. & Biol.,vol. 29, No. 12, pp. 1749-1757 (Jul. 2003).

Chen et al., "Efficient Gene Delivery to Pancreatic Islets with Ultrasonic Microbubble Destruction Technology," PNAS, vol. 103, No. 22, pp. 8469-8474 (May 30, 2006).
Chen et al., "Multiple Acoustical Matching Layer Design of Ultrasonic Transducer for Medical Application," Jpn. J. Appl. Phys., vol. 41, pp. 6098-6107 (Oct. 2002).
Choi et al., "Spatio-Temporal Analysis of Molecular Delivery Through the Blood-Brain Barrier Using Focused Ultrasound," Physics in Medicine and Biology, vol. 52, pp. 5509-5530 (2007).
Choi et al., "Spatiotemporal evolution of cavitation dynamics exhibited by flowing microbubbles during ultrasound exposure," The Journal of te Acoustical Society of America, vol. 132, pp. 3538-3549 (2012).
Choi et al., "Noninvasive, Transcranial and Localized Opening of the Blood-Brain Barrier Using Focused Ultrasound in Mice," Ultrasound in Medicine and Biology, vol. 33, No. 1, pp. 95-104 (2007).
Chomas et al., "Threshold of Fragmentation for Ultrasonic Contrast Agents," Journal of Biomedical Optics, vol. 6, No. 2, pp. 141-150 (Apr. 2001).
Chomas et al., "Mechanisms of Contrast Agent Destruction," IEEE Transactions Ultrasonics, Ferroelectrics, and Frequency Control, vol. 48, No. 1, pp. 232-248 (Jan. 2001).
Chomas et al., "Optical Observation of Contrast Agent Destruction," Applied Physics Letters, vol. 77, No. 7, pp. 1056-1058 (Aug. 14, 2000).
Chopra et al., "Multifrequency Ultrasound Transducers for Conformal Interstitial Thermal Therapy," IEEE Transactions on Ultrasonics, Ferroelectrics, and Frequency Control, vol. 50, No. 7, pp. 881-889 (Jul. 2003).
Clarke et al., "Production of harmonics in vitro by high-intensity focused ulrasound," Ultrasound in Medicine Biology, vol. 25, pp. 1417-1424 (1999).
Coakley et al., "Ultrasonic Manipulation of Particles and Cells," Bioseparation, vol. 4, pp. 73-83 (1994).
Coussios et al., "Applications of acoustics and cavitation to non-invasive therapy and drug delivery," Annual Review of Fluid Mechanics, vol. 40, pp. 395-420 (2008).
Couture et al., "Ultrasound inernal tattooing," Medical Physics, vol. 38, pp. 1116-1123 (2011).
Couture et al., "A Model for Reflectivity Enhancement Due to Surface Bound Submicrometer Particles," Ultrasound in Medicine & Biology, vol. 32, No. 8, pp. 1247-1255 (May 2006).
Couture et al., "Investigating Perfluorohexane Particles with High-frequency Ultrasound," Ultrasound in Medicine & Biology, vol. 32, No. 1, pp. 73-82 (Sep. 2005).
Cronin et al., "Comprehensive Next-Generation Cancer Genome Sequencing in the Era of Targeted Therapy and Personalized Oncology," Biomarkers Med.; 5(3), pp. 293-305 (2011).
Crowder et al., "Sonic Activation of Molecularly-Targeted Nanoparticles Accelerates Transmembrane Lipid Delivery to Cancer Cells Through Contact-mediated Mechanisms: Implications for Enhanced Local Drug Delivery," Ultrasound in Medicine & Biology, vol. 31, No. 12, pp. 1693-1700 (2005).
Crum, Lawrence A., "Bjerknes Forces on Bubbles in a Stationary Sound Field," The Journal of the Acoustical Society of America, vol. 57, No. 6, Part 1, pp. 1363-1370 (1975).
Crum et al., "The Motion of Bubbles in a Stationary Sound Field," The Journal of the Acoustical Society of America, p. 1411 (1969).
Culp et al., "Successful Microbubble Sonothrombolysis Without Tissue Plasminogen Activator in a Rabbit Model of Acute Ischemic Stroke," Stroke, vol. 42, No. 8, pp. 1-15 (Aug. 2011).
D'Astous et al., "Frequency dependence of ultrasound attenuation and backscatter in breast tissue," Ultrasound in Medicine Biology, vol. 12, pp. 795-808 (1986).
Dayton et al., "Molecular ultrasound imaging using microbubble contrast agents," Frontiers in Bioscience, vol. 12, pp. 5124-5142 (Sep. 1, 2007).
Dayton et al., "Application of Ultrasound to Selectively Localize Nanodroplets for Targeted Imaging and Therapy," Molecular Imaging, vol. 5, No. 3, pp. 1-32 (Jul. 2006).
Dayton et al., "Ultrasound-Mediated Therapies Using Oil and Perfluorocarbon-Filled Nanodroplets," Drug Development Research, vol. 67, pp. 42-46 (2006).

(56) References Cited

OTHER PUBLICATIONS

Dayton et al., "Ultrasonic Analysis of Peptide- and Antibody-Targeted Microbubble Contrast Agents for Molecular Imaging of αvβ3-expressing Cells," Molecular Imaging, vol. 3, No. 2, pp. 1-18 (Apr. 2004).
Dayton et al., "Targeted Imaging Using Ultrasound," Journal of Magnetic Resonance Imaging, vol. 16, pp. 362-377 (2002).
Dayton et al., "The Magnitude of Radiation Force on Ultrasound Contrast Agents," The Journal of the Acoustical Society of America, vol. 112, No. 5, Part 1, pp. 2183-2192 (2002).
Dayton et al., "Optical and Acoustical Dynamics of Microbubble Contrast Agents Inside Neutrophils," Biophysical Journal, vol. 80, pp. 1547-1556 (Mar. 2001).
Dayton et al., "Acoustic Radiation Force in Vivo: A Mechanism to Assist Targeting of Microbubbles," Ultrasound in Med. and Biol. vol. 25, No. 8, pp. 1195-1201 (1999).
Dayton et al., "Optical and Acoustical Observations of the Effects of Ultrasound on Contrast Agents," IEEE Transactions on Ultrasonics, Ferroelectrics, and Frequency Control,vol. 46, No. 1, pp. 220-232 (Jan. 1999).
Dayton et al., "A Preliminary Evaluation of the Effects of Primary and Secondary Radiation Forces on Acoustic Contrast Agents," IEEE Transactions on Ultrasonics, Ferroelectrics, and Frequency Control, vol. 44, No. 6, pp. 1264-1277 (Nov. 1997).
Dayton et al., "Action of Microbubbles When Insonified: Experimental Evidence," IEEE Ultrasonics Symposium, vol. 2, pp. 1131-1134 (1996).
Deininger, "Random Subcloning if Sonicated DNA: Application to Shotgun DNA Sequence Analysis," Analytical Biochemistry, vol. 129(1), pp. 216-223 (1983).
Deng et al., "Ultrasound-Induced Cell Membrane Porosity," Ultrasound in Medicine & Biology, vol. 30, No. 4, pp. 519-526 (2004).
Desilets et al., "Design of Efficient Broad-Band Piezoelectric Transducers," IEEE Transactions on Sonics and Ultrasonics, vol. SU-25, No. 3, pp. 115-125 (May 1978).
Doinikov et al., "Modeling of Nonlinear Viscous Stress in Encapsulating Shells of Lipid-Coated Contrast Agent Microbubbles," Ultrasonics, vol. 49, No. 2, pp. 1-17 (Feb. 2009).
Doinikov et al., "Resonance Frequencies of Lipid-Shelled Microbubbles in the Regime of Nonlinear Oscillations," Ultrasonics, vol. 49, No. 2, pp. 1-16 (Feb. 2009).
Doinikov et al., "Modeling of the Acoustic Response From Contrast Agent Microbubbles Near a Rigid Wall," Ultrasonics, vol. 49, No. 2, pp. 1-17 (Feb. 2009).
Doinikov et al., "Maxwell Rheological Model for Lipid-Shelled Ultrasound Microbubble Contrast Agents," The Journal of the Acoustical Society of America, vol. 121, No. 6, pp. 1-26 (Jun. 2007).
Doinikov et al., "Spatio-temporal Dynamics of an Encapsulated Gas Bubble in an Ultrasound Field," The Journal of the Acoustical Society of America, vol. 120, No. 2, pp. 1-25 (Aug. 2006).
Dromi et al., "Pulsed-High Intensity Focused Ultrasound and Low Temperature Sensitive Liposomes for Enhanced Targeted Drug Delivery and Antitumor Effect," Clinical Cancer Research, vol. 13, pp. 2722-2727 (2007).
Ellegala et al., "Imaging Tumor Angiogenesis with Contrast Ultrasound and Microbubbles Targeted to αvβ3," Circulation, Journal of the American Heart Association, vol. 108 pp. 336-341 (2003).
Eshpuniyani et al., "A boundary element model of microbubble sticking and sliding in the microcirculation," International Journal of Heat and Mass Transfer, vol. 51, pp. 5700-5711 (2008).
Evans et al., "Physical Properties of Phase-Change Emulsions," Langmuir, vol. 22, pp. 9538-9545 (Sep. 2006).
Fabiilli et al., "Delivery of Chloranbucil Using an AcousticallyTriggered Perfluoropentane Emulsion," Ultrasound in Medicine and Biology, vol. 36, No. 8, pp. 1-25 (Aug. 2010).
Fabiilli et al., "Delivery of Water-Soluble Drugs Using Acoustically Triggered Perfluorocarbon Double Emusions," Pharm. Res., vol. 27, No. 12, pp. 1-25 (Dec. 2010).

Fabiilli et al., "The Role of Inertial Cavitation in Acoustic Droplet Vaporization," IEEE Transactions on Ultrasonics, Ferroelectrics, and Frequency Control, vol. 56, No. 5, pp. 1-24 (May 2009).
Farook et al., "Controlling Size and Size Distribution of Electrohydrodynamically Prepared Microbubbles," Bubble Science, Engineering and Technology, vol. 1, No. 1/2, pp. 53-57 (2009).
Farook et al., "Preparation of Suspensions of Phospholipid-coated Microbubbles by Coaxial Electrohydrodynamic Atomization," The Journal of the Royal Society Interface, vol. 6, (32), pp. 271-277 (Jul. 2008).
Ferrara, "Driving Delivery Vehicles with Ultrasound," Advanced Drug Delivery Reviews, vol. 60, No. 10, pp. 1-9 (Jun. 30, 2008).
Ferrara et al., "Ultrasound Microbubble Contrast Agents: Fundamentals and Application to Gene and Drug Delivery," The Annual Review of Biomedical Engineering, vol. 9, pp. 415-447 (2007).
Ferretti et al., "Tumor Interstitial Fluid Pressure as an Early-Response Marker for Anticancer Therapeutics," Neoplasia, vol. 11, No. 9, pp. 874-881 (Sep. 2009).
Feshtan et al., "Microbubble Size Isolation by Differential Centrifugation," Journal of Colloid and Interface Science, 329, pp. 316-324 (2009).
Forsberg et al., "Subharmonic imaging of contrast agents," Ultrasonics, vol. 38, pp. 93-98 (2000).
Ganan-Calvo et al., "Perfectly Monodisperse Microbubbling by Capillary Flow Focusing," Physical Review Letters, vol. 87, No. 27, pp. 274501-1-274501-4 (2001).
Gao et al., "Drug-Loaded Nano/Microbubbles for Combining Ultrasonography and Targeted Chemotherapy," Ultrasonics, vol. 48, No. 4, pp. 1-24 (Aug. 2008).
Garstecki et al., "Formation of Bubbles and Droplets in Microfluidic Systems," Bulletin of the Polish Academy of Sciences, vol. 53, No. 4, pp. 361-372 (2005).
Gessner et al., "High-Resolution, High-Contrast Ultrasound Imaging Using a Prototype Dual-Frequency Transducer: In Vitro and In Vivo Studies," IEEE Transactions on Ultrasonics, Ferroelectrics, and Frequency Control, vol. 57, No. 8, pp. 1772-1781 (Aug. 2010).
Gessner et al., "Advances in Molecular Imaging with Ultrasound," Mol Imaging , vol. 9, No. 3, pp. 1-21 (Jun. 2010).
Gessner et al., "Radiation Force-Enhanced Targeted Imaging and Near Real-time Molecular Imaging Using a Dual-Frequency High-Resolution Transducer: In-vitro and In-vivo Results," Proceedings of the 2009 IEEE Ultrasonics Symposium, In Press, pp. 1-4, (2009).
Giesecke et al., "Ultrasound-Mediated Cavitation Thresholds of Liquid Perfluorocarbon Droplets in Vitro," Ultrasound in Medicine & Biology, vol. 29, No. 9, pp. 1359-1365 (2003).
Gingrich et al., "Partial CviJI Digestion as an Alternative Approach to Generate Cosmid Sublibraries for Large-Scale Sequencing Projects," Biotechniques, vol. 21 (1), pp. 99-104 (1996).
Giresi et al., "Isolation of Active Regulatory Elements from Eukaryotic Chromatin Using FAIRE (Formaldehyde Assisted Isolation of Regulatory Elements)," Methods, vol. 48, No. 3, pp. 1-13 (Jul. 2009).
Goldberg et al. (eds), "Radiological Application of Contrast, in Ultrasound Contrast Agents," London, Part III, pp. 239-3360 (2001).
Goll, "Design of Broad-Band Fluid-Loaded Ultrasonic Transducers," IEEE Transactions on Sonics and Ultrasonics, vol. SU-26, No. 6, pp. 385-393 (Nov. 1979).
Gramiak et al., "Echocardiography of the aortic root," Invest. Radiol., vol. 3, pp. 356-366 (1968).
Groschl, "Ultrasonic Separation of Suspended Particles—Part I: Fundamentals," Acustica, vol. 84, pp. 432-447 (1998).
Haworth et al., "Towards Aberration Correction of Transcranial Ultrasound Using Acoustic Droplet Vaporization," Ultrasound Med Biol, vol. 34, No. 3, pp. 1-24 (Mar. 2008).
Hengen, "Shearing DNA for Genomic Library Construction," Trends in Biochemical Sciences, vol. 22, pp. 273-274 (1997).
Hettiarachchi et al., "Controllable Microfluidic Synthesis of Multiphase Drug-Carrying Liposheres for Site-Targeted Therapy," Biotechnology Progress, vol. 25, No. 4, pp. 1-17 (2009).
Hettiarachchi et al., "On-chip Generation of Microbubbles as a Practical Technology for Manufacturing Contrast Agents for Ultrasonic Imaging," Lab Chip., vol. 7, No. 4, pp. 1-14 (Apr. 2007).

(56) References Cited

OTHER PUBLICATIONS

Hitchcock et al., "Ultrasound-Assisted Thrombolysis for Stroke Therapy: Better Thrombus Break-up with Bubbles," Stroke, vol. 41, pp. 1-8 (Oct. 2010).
Hobbs et al., "Regulation of Transport Pathways in Tumor Vessels: Role of Tumor Type and Microenvironment," Proceedings of the National Academy of Sciences, vol. 95, No. 8, pp. 4607-4612 (Apr. 1998).
Hoff et al., "Oscillations of Polymeric Microbubbles: Effect of the Encapsulating Shell," The Journal of the Acoustical Society of America, vol. 107, No. 4, pp. 2272-2280 (2000).
Hoffman et al., "Genome-Wide Identification of DNA-Protein Interactions Using Chromatin Immunoprecipitation Coupled with Flow Cell Sequencing," Journal of Endocrinology, vol. 201(1), pp. 1-13 (2009).
Hoheisel et al., "Control of Partial Digestion Combining the Enzymes dam Methylase and MboI," Nucleic Acids Research, vol. 17, No. 23, pp. 9571-9582 (1989).
Hopp et al., "Factory Physics, Foundations of Manufacturing Management," Second Edition, Chapter 7, pp. 213-227 (2008).
Huh et al., "A Gravity-Driven Microfluidic Particle Sorting Device with Hydrodynamic Separation Amplification," Analytical Chemistry, vol. 79, pp. 1-14 (Feb. 2007).
Hurrell, "Voltage to pressure conversion: are you getting 'phased' by the problem?," Journal of Physics: Conference Series, vol. 1, p. 57 (2004).
Hynynen et al., "Local and Reversible Blood-Brain Barrier Disruption by Noninvasive Focused Ultrasound at Frequencies Suitable for Trans-skull Sonications," NeuroImage, vol. 24, pp. 12-20 (2005).
Iyer et al., "Exploiting the Enhanced Permeability and Retention Effect for Tumor Targeting," Drug Discovery Today, vol. 11, No. 17/18, pp. 812-818 (2006).
Janzen et al., "Epigenetics: Tools and Technologies," Drug Discov Today Technol., vol. 7, No. 1, pp. 1-13 (2010).
Janzen et al., "High Throughput Screening. Methods and Protocols, Second Edition," (2009).
Janzen et al., "Review: Advances in Improving the Quality and Flexibility of Compound Management," Journal of Biomolecular Screening, vol. 14, No. 5, pp. 444-451 (2009).
Janzen, "High Throughput Screening: Methods and Protocols," (2002).
Jayaweera et al., "In Vivo Myocardial Kinetics of Air-Filled Albumin Microbubbles During Myocardial Contrast Echocardiography. Comparison with Radiolabeled Red Blood Cells," Circulation Research—The Journal of the American Heart Association, vol. 74, No. 6, pp. 1157-1165 (1994).
Jones et al., "Prospective Thermal Dosimetry: The Key to Hyperthermia's Future," International Journal of Hyperthermia, vol. 22, No. 3, pp. 247-253 (May 2006).
Ten Kate et al., "Molecular imaging of inflammation and intraplaque vasa vasorum: a step forward to identification of vulnerable plaques? ," J. Nucl. Cardiol., vol. 17, pp. 897-912 (2010).
Kawabata et al., "Nanoparticles with Multiple Perfluorocarbons for Controllable Ultrasonically Induced Phase Shifting," Japanese Journal of Applied Physics, vol. 44, No. 6B, pp. 4548-4552 (2005).
Kaya et al., "Acoustic Responses of Monodisperse Lipid Encapsulated Microbubble Contrast Agents Produced by Flow Focusing," Bubble Science, Engineering and Technolology, vol. 2, No. 2, pp. 33-40 (Dec. 2010).
Kaya et al., "Changes in Lipid-Encapsulated Microbubble Population During Continuous Infusion and Methods to Maintain Consistency," Ultrasound in Medicine & Biology, vol. 35, No. 10, pp. 1-16 (Oct. 2009).
Klibanov, "Microbubble Contrast Agents—Targeted Ultrasound Imaging and Ultrasound-Assisted Drug-Delivery Applications," Investigative Radiology, vol. 41, No. 3, pp. 354-362 (2006).
Klibanov et al., "Targeting and Ultrasound Imaging of Microbubble-based Contrast Agents," Magnetic Resonance Materials in Physics, Biology, and Medicine, vol. 8, pp. 177-184 (1999).
Klibanov et al., "Targeting of Ultrasound Contrast Material. An in vitro Feasibility Study," Acta Radiologica, Supplement 412, pp. 113-120 (1997).
Knierim et al., "Systematic Comparison of Three Methods for Fragmentation of Long-range PCR Products for Next Generation Sequencing," PLoS ONE, vol. 6, Issue 11, e28240, pp. 1-6 (Nov. 2011).
Kripfgans et al., "Acoustic Droplet Vaporization for Temporal and Spatial Control of Tissue Occlusion: A Kidney Study," IEEE Transactions on Ultrasonics, Ferroelectrics, and Frequency Control, vol. 52, No. 7, pp. 1101-1110 (2005).
Kripfgans et al., "On the Acoustic Vaporization of Micrometer-Sized Droplets," The Journal of the Acoustical Society of America, vol. 116, No. 1, pp. 272-281 (2004).
Kripfgans et al., "In Vivo Droplet Vaporization for Occlusion Therapy and Phase Aberration Correction," IEEE Transactions on Ultrasonics, Ferroelectrics, and Frequency Control, vol. 49, pp. 726-738 (2002).
Kripfgans et al., "Acoustic Droplet Vaporization for Therapeutic and Diagnostic Applications," Ultrasound in Med. & Biol., vol. 26, No. 7, pp. 1177-1189 (2000).
Krishnan et al., "Inertial lift on a Moving Sphere in Contact with a Plane Wall in a Shear Flow," Phys. Fluids, vol. 7, No. 11, pp. 2538-2545 (1995).
Kruse et al., "Spatial and Temporal-Controlled Tissue Heating on a Modified Clinical Ultrasound Scanner for Generating Mild Hyperthermia in Tumors" IEEE Transactions on Biomedical Engineering, vol. 57, No. 1, pp. 155-166 (Jan. 2010).
Kruse et al., "A New Imaging Strategy Using Wideband Transient Response of Ultrasound Contrast Agents," IEEE Transactions on Ultrasonics, Ferroelectrics and Frequency Control, vol. 52, No. 8, pp. 1-22 (Aug. 2005).
Kwan et al., "Microbubble Dissolution in a Multigas Environment," Langmuir, vol. 26, No. 9 pp. 6542-6548 (2010).
Lamberti et al., "A New Approach for the Design of Ultrasono-Therapy Transducers," IEEE Transactions on Ultrasonics, Ferroelectrics, and Frequency Control, vol. 44, No. 1, pp. 77-84 (Jan. 1997).
Landmark et al., "Pharmacokinetics of Perfluorobutane Following Intravenous Bolus Injection and Continuous Infusion of Sonazoid™ in Healthy Volunteers and in Patients with Reduced Pulmonary Diffusing Capacity," Ultrasound in Med. & Biol., vol. 34, No. 3, pp. 494-501 (2008).
"Definity®," Lantheus Medical Imaging. Wayback Machine https://web.archive.org/web/20101123011336/http://www.definityimaging.com/main.html? (Nov. 23, 2010).
Lanza et al., "Targeted Ultrasonic Contrast Agents for Molecular Imaging and Therapy," Current Problems in Cardiology, pp. 625-653 (Dec. 2003).
Lanza et al., "High-Frequency Ultrasonic Detection of Thrombi with a Targeted Contrast System," Ultrasound in Med. & Biol., vol. 23, No. 6, pp. 863-870 (1997).
Lanza et al., "A Novel Site—Targeted Ultrasonic Contrast Agent with Broad Biomedical Application," Circulation, vol. 94. pp. 1-9 (1996).
Lediju et al., "Short-lag spatial coherence imaging," 2010 IEEE International Ultrasonics Symposium, pp. 987-990 (2010).
Lee et al., "Oscillatory Vaporization and Acoustic Response of Droplet at High Pressure," International Communications in Heat and Mass Transfer, vol. 35, No. 10, pp. 1302-1306 (2008).
Leong-Poi et al., "Noninvasive Assessment of Angiogenesis by Ultrasound and Microbubbles Targeted to αv-Integrins," Circulation—Journal of the American Heart Association, vol. 107, pp. 455-460 (2003).
Lindner, "Contrast Ultrasound Molecular Imaging of Inflammation in Cardiovascular Disease," Cardiovascular Research, vol. 84, pp. 182-189 (2009).
Lindner, "Microbubbles in Medical Imaging: Current Applications and Future Directions," Nature Reviews—Drug Discovery, vol. 3, pp. 527-532 (Jun. 2004).
Lindner, "Evolving Applications for Contrast Ultrasound," The American Journal of Cardiology, vol. 90, No. 10A, pp. 72J-80J (2002).

(56) References Cited

OTHER PUBLICATIONS

Lindner et al., "Delivery of Drugs with Ultrasound," Echocardiography, vol. 18, No. 4, pp. 329-337 (May 2001).
Lindner et al., "Assessment of Resting Perfusion with Myocardial Contrast Echocardiography: Theoretical and Practical Considerations," The American Heart Journal, vol. 139, No. 2, Part 1, pp. 231-240 (2000).
Lindner et al., "Noninvasive Ultrasound Imaging of Inflammation Using Microbubbles Targeted to Activated Leukocytes," Circulation—Journal of the American Heart Association, vol. 102, No. 22, pp. 2745-2750 (2000).
Linker et al., "In Vivo Molecular Imaging of Adhesion Molecules in Experimental Autoimmune Encephalomyelitis (EAE)," Journal of Autoimmunity, vol. 25, pp. 199-205 (2005).
Lo et al., "Acoustic Droplet Vaporization Threshold: Effects of Pulse Duration and Contrast Agent," IEEE Transactions on Ultrasonics, Ferroelectrics, and Frequency Control, vol. 54, No. 5, pp. 933-946 (2007).
Lo et al., "Spatial Control of Gas Bubbles and Their Effects on Acoustic Fields," Ultrasound Med Biol., vol. 32, No. 1, pp. 95-106 (2006).
Lockwood et al., "Modeling and Optimization of High-Frequency Ultrasound Transducers," IEEE Transactions on Ultrasonics, Ferroelectrics, and Frequency Control, vol. 41, No. 2, pp. 225-230 (Mar. 1994).
Lum et al., "Ultrasound Radiation Force Enables Targeted Deposition of Model Drug Carriers Loaded on Microbubbles," Journal of Controlled Release, vol. 111, No. 1-2, pp. 1-15 (Mar. 2006).
Macedo et al., "Acoustic Effects on Gas Bubbles in the Flows of Viscous Fluids and Whole Blood," The Journal of the Acoustical Society of America, vol. 53, No. 5, pp. 1327-1335 (1973).
Marmottant et al., "A Model for Large Amplitude Oscillations of Coated Bubbles Accounting for Buckling and Rupture," The Journal of the Acoustical Society of America, vol. 118, No. 6, pp. 3499-3505 (2005).
Marsh et al., "Molecular Imaging with Targeted Perfluorocarbon Nanoparticles: Quantification of the Concentration Dependence of Contrast Enhancement for Binding to Sparse Cellular Epitopes," Ultrasound Med Biol., vol. 33, No. 6, pp. 1-16 (Jun. 2007).
Martin et al., "Current status and prospects for microbubbles in ultrasound theranostics," Wiley Interdisciplinary Reviews: Nanomedicine and Nanobiotechnology, vol. 5. pp. 329-345 (2013).
Martz et al., "Precision Manufacture of Phase-Change Perflurocarbon Droplets Using Microfluidics," Ultrasound Med Biol., vol. 37, No. 11, pp. 1-13 (Nov. 2011).
Matsuura et al., "Nanoparticle-Loaded Perfluorocarbon Droplets for Imaging and Therapy," IEEE International Ultrasonics Symposium (IUS), pp. 5-8 (2009).
Mattrey, "The Potential Role of Perfluorochemicals (PFCS) in Diagnostic Imaging," Artificial Cells, Blood Substitutes, and Immobilization Biotechnology, vol. 22, No. 2, pp. 295-313 (1994).
McKeighen, "Design Guidelines for Medical Ultrasonic Arrays," SPIE, vol. 3341, pp. 1-18 (1998).
Meairs et al., "Microbubbles for Thrombolysis of Acute Ischemic Stroke," Cerebrovascular Diseases, vol. 27, pp. 55-65 (Apr. 16, 2009).
Meyer et al., "Freestream Nuclei and Traveling-Bubble Cavitation," Transactions of the ASME, vol. 114, pp. 672-679 (Dec. 1992).
Meyerson et al., "Advances in Understanding Cancer Genomes Through Second-Generation Sequencing," Nature Reviews, Genetics, vol. 11, pp. 685-696 (Oct. 2010).
Miller et al., "Bioeffects Considerations for Diagnostic Ultrasound Contrast Agents," J Ultrasound Med, vol. 27, pp. 611-632 (2008).
Miller et al., "Lysis and Sonoporation of Epidermoid and Phagocytic Monolayer Cells by Diagnostic Ultrasound Activation of Contrast Agent Gas Bodies," Ultrasound in Medicine and Biology, vol. 27, No. 8, pp. 1107-1113 (2001).
Miller et al., "Sonoporation of Monolayer Cells by Diagnostic Ultrasound Activation of Contrast-Agent Gas Bodies," Ultrasound in Medicine and Biology, vol. 26, No. 4, pp. 661-667 (2000).
Miller et al., "Cavitation Nucleation Agents for Nonthermal Ultrasound Therapy," Journal of the Acoustical Society of America, vol. 107, No. 6, pp. 3480-3486 (Jun. 2000).
Miller et al., "Sonoporation of Cultured Cells in the Rotating Tube Exposure System," Ultrasound in Medicine and Biology, vol. 25, No. 1, pp. 143-449 (1999).
Minnaert, "On musical air-bubbles and the sounds of running water," Philosophical Magazine, vol. 16, pp. 235-248 (1933).
Misaridis et al., "Use of modulated excitation signals in medical ultrasound. Part 1: Basic concepts and expected benefits," IEEE Transactions on Ultrasonics Ferroelectronics and Frequency Control, vol. 52, pp. 177-191 (2005).
Mitragotri, "Healing Sound: The Use of Ultrasound in Drug Delivery and Other Theraputic Applications," Nature Reviews, Drug Discovery, vol. 4, pp. 255-260 (Mar. 2005).
Morgan, "Experimental and Theoretical Evaluation of Ultrasonic Contrast Agent Behavior," Dissertation, University of Virginia, (Jan. 2001).
Morgan et al., "Experimental and Theoretical Evaluation of Microbubble Behavior: Effect of Transmitted Phase and Bubble Size," IEEE Transactions on Ultrasonics, Ferroelectrics, and Frequency Control, vol. 47, No. 6, pp. 1494-1509 (Nov. 2000).
Morgan et al., "Experimental and Theoretical Analysis of Individual Contrast Agent Behavior," IEEE Ultrasonics Symposium, vol. 2, pp. 1685-1688 (1999).
Morgan et al., "Changes in the Echoes from Ultrasonic Contrast Agents with Imaging Parameters," IEEE Transactions on Ultlrasonics, Ferroelectrics, and Frequency Control, vol. 45, No. 6, pp. 1537-1548 (Nov. 1998).
Mullin et al., "Effect of Anesthesia Carrier Gas on In-Vivo Circulation Times of Ultrasound Microbubble Contrast Agents in Rats," Contrast Media Mol Imaging, vol. 6, No. 3, pp. 1-14 (2011).
Mulvagh et al., "Contrast Echocardiography: Current and Future Applications," Journal of the American Society of Echocardiography, vol. 13, No. 4, pp. 331-342 (Apr. 2000).
Needles et al., "Nonlinear contrast imaging with an array-based micro-ultrasound system," Ultrasound in Medicine & Biology, vol. 36, pp. 2097-2106 (2010).
Nyborg, "Solutions of the Bio-Heat Transfer Equation," Physics in Medicine and Biology, vol. 33, No. 7, pp. 785-792 (1988).
Oakley, "Calculation of Ultrasonic Transducer Signal-to-Noise Rations Using the KLM Model," IEEE Transactions on Ultrasonics, Ferroelectrics, and Frequency Control, vol. 44, No. 5, pp. 1018-1026 (Sep. 1997).
Oefner et al., "Efficient Random Subcloning of DNA Sheared in a Recirculating Point-Sink Flow System," Nucleic Acids Research, vol. 24, No. 20, pp. 3879-3886 (1996).
Okpodu et al., "Rapid Isolation of Nuclei From Carrot Suspension Culture Cells Using a BioNebulizer," BioTechniques, vol. 16, No. 1, pp. 154-158 (1994).
Osoegawa et al., "A Bacterial Artificial Chromosome Library for Sequencing the Complete Human Genome," Genome Research, vol. 11, No. 3, pp. 483-496 (2001).
Pan et al., "Study of Sonoporation Dynamics Affected by Ultrasound Duty Cycle," Ultrasound in Medicine and Biology, vol. 31, No. 6, pp. 849-856 (2005).
Pan et al., "Sonoporation of Cells for Drug and Gene Delivery," Conf Proc IEEE Eng Med Biol Soc, vol. 5, pp. 3531-3534 (2004).
Pancholi et al., "Novel Methods for Preparing Phospholipid Coated Microbubbles," Eur. Blophys. J., vol. 37, pp. 515-520 (2008).
Pancholi et al., "Generation of Microbubbles for Diagnostic and Therapeutic Applications Using a Novel Device," Journal of Drug Targeting, vol. 16, No. 6, pp. 494-501 (Jul. 2008).
Park et al., "Unsteady Forces on Spherical Bubbles," Experimnets in Fluids, vol. 19, pp. 167-172 (1995).
Patil et al., "Particle Diameter Influences Adhesion Under Flow," Biophysical Journal, vol. 80, pp. 1733-1743 (Apr. 2001).
Pitt et al., "Phase Transitions of Perfluorocarbon Nanoemulsion Induced with Ultrasound: A Mathematical Model," Ultrasonics Sonochemistry, vol. 21, pp. 879-891 (2014).
Pitt et al., "Ultrasonic Drug Delivery—A General Review," Expert Opinion on Drug Delivery, vol. 1, pp. 1-32 (Nov. 2004).

(56) References Cited

OTHER PUBLICATIONS

Plesset et al., "Bubble Dynamics and Cavitation," Annu. Rev. Fluid Mech., vol. 9, pp. 145-185 (1977).
Popa-Burke et al., "Streamlined System for Purifying and Quantifying a Diverse Library of Compounds and the Effect of Compound Concentration Measurements on the Accurate Interpretation of Biological Assay Results," Analytical Chemistry, vol. 76, No. 24, pp. 7278-7287 (Dec. 15, 2004).
Price et al., "Delivery of Colloidal Particles and Red Blood Cells to Tissue Through Microvessel Ruptures Created by Targeted Microbubble Destruction with Ultrasound," Journal of the American Heart Association, vol. 98, pp. 1264-1267 (Sep. 29, 1998).
Prosperetti, "Bubble Phenomena in Sound Fields: Part Two," Ultrasonics, vol. 22, pp. 115-124 (May 1984).
Qamar et al., "Dynamics of Acoustic Droplet Vaporization in Gas Embolotherapy," Applied Physics Letters, vol. 96, pp. 143702-1-143702-3 (2010).
Qamar et al., "Evolution of acoustically vaporized microdroplets in gas embolotherapy," Journal of Biomechanical Engineering, vol. 134, pp. 031010-1-031010-13 (2012).
Rapoport, "Phase-shift, stimuli-responsive perfluorocarbon nanodroplets for drug delivery to cancer," Wiley Interdisciplinary Reviews: Nanomedicine and Nanobiotechnology, vol. 4, pp. 492-510 (2012).
Rapoport et al., "Ultrasound-mediated tumor imaging and nanotherapy using drug loaded, block copolymer stabilized perfluorocarbon nanoemulsions," Journal of Controlled Release, vol. 153, pp. 4-15 (2011).
Rapoport et al., "Cavitation Properties of Block Copolymer Stabilized Phase-Shift Nanoemulsions Used as Drug Carriers," Ultrasound Med Biol, vol. 36, No. 3, pp. 1-21 (Mar. 2010).
Rapoport et al., "Controlled and Targeted Tumor Chemotherapy by Ultrasound-activated Nanoemulsions/Microbubbles," J Control Release, vol. 138, No. 3, pp. 1-25 (Sep. 15, 2009).
Rapoport et al., "Microbubble Generation in Phase-Shift Nanoemulsions Used as Anticancer Drug Carriers," Bubble Sci Eng Technol, vol. 1, pp. 1-21 (2009).
Rapoport et al., "Multifunctional Nanoparticles for Combining Ultrasonic Tumor Imaging and Targeted Chemotherapy," J Natl Cancer Inst, vol. 99, pp. 1095-1106 (2007).
Reddy et al., "Coupled Dynamics of Translation and Collapse of Acoustically Driven Microbubbles," J. Acoust. Soc. Am., vol. 112, No. 4, pp. 1346-1352 (Oct. 2002).
Reinhardt et al., "Ultrasound Derived Imaging and Quantification of Cell Adhesion Molecules in Experimental Autoimmune Encephalomyelitis (EAE) by Sensitive Particle Acoustic Quantification (SPAQ)," NeuroImage, vol. 27, pp. 267-278 (2005).
Reznik et al., "The efficiency and stability of bubble formation by acoustic vaporization of submicron perfluorocarbon droplets," Ultrasonics, vol. 53, pp. 1368-1376 (2013).
Reznik et al., "Investigation of Vaporized Submicron Perfluorocarbon Droplets as an Ultrasound Contrast Agent," Ultrasound in Medicine & Biology, vol. 37, pp. 1271-1279 (2011).
Roe, "Shotgun Library Construction for DNA Sequencing," Methods in Molecular Biology, vol. 255, pp. 171-187 (2004).
Rychak et al., "Enhanced Targeting of Ultrasound Contrast Agents Using Acoustic Radiation Force," Ultrasound in Medicine and Biology, vol. 33, No. 7, pp. 1132-1139 (Jul. 2007).
Rychak et al., "Acoustic Radiation Force Enhances Targeted Delivery of Ultrasound Contrast and Microbubbles: In Vitro Verification," IEEE Transactions on Ultrasonics, Ferroelectrics, and Frequency Control, vol. 52, No. 3, pp. 421-433 (Mar. 2005).
Rychak et al., "Deformable Gas-Filled Microbubbles Targeted to P-Selectin," Journal of Controlled Release, vol. 114, pp. 288-299 (2006).
Salgaonkar et al., "Passive cavitation imaging with ultrasound arrays," The Journal of the Acoustical Society of America, vol. 126, pp. 3071-3083 (2009).
Sassaroli et al., "Cavitation threshold of microbubbles in gel tunnels by focused ultrasound," Ultrasound in Medicine Biology, vol. 33, pp. 1651-1660 (2007).

Sboros et al., "The Assessment of Microvascular Flow and Tissue Perfusion Using Ultrasound Imaging," Proceedings of the Institution of Mechanical Engineers, Part H: Journal of Engineerying in Medicince, vol. 224, pp. 273-290 (2010).
Sboros, "Response of Contrast Agents to Ultrasound," Advanced Drug Delivery Reviews, No. 60, pp. 1117-1136 (Mar. 2008).
Schad et al., "In Vitro Characterization of Perfluorocarbon Droplets for Focused Ultrasound Therapy," Physics in Medicine and Biology, vol. 55, pp. 4933-4947 (2010).
Schoppee et al., "Chromatin Immunoprecipitation (ChiP): Revisiting the Efficacy of Sample Preparation, Sonication, Quantification of Sheared DNA, and Analysis via PCR," PLoS ONE, vol. 6, Issue 10, e26015, pp. 1-10 (Oct. 2011).
Schroeder et al., "Ultrasound Triggered Release of Cisplatin from Liposomes in Murine Tumors," Journal of Controlled Release, vol. 137, pp. 63-68 (2009).
Schumann et al., "Targeted-Microbubble Binding Selectively to GPIIb IIIa Receptors of Platelet Thrombi," Investigative Radiology, vol. 37, No. 11, pp. 587-593 (Nov. 2002).
Seed et al., "Representation of DNA Sequences in Recombinant DNA Libraries Prepared by Restriction Enzyme Partial Digestion," Gene, vol. 19, pp. 201-209 (Jun. 1982).
Selfridge et al., "KLM Transducer Model Implementation Using Transfer Matrices," IEEE Ultrasonics Symposium, pp. 875-877 (1985).
Sheeran et al., "Vaporization phenomena for ultrasound phase-change contrast agents assessed via high-speed optical microscopy," 2013 IEEE International Ultrasonics Symposium (IUS), pp. 1841-1844 (Jul. 21-25, 2013).
Sheeran et al., "Toward ultrasound molecular imaging with phase-change contrast agents: an in vitro proof of principle," Ultrasound Med. Biol., vol. 39, No. 5, pp. 893-902 (May 2013).
Sheeran et al., "Phase-transition thresholds and vaporization phenomena for ultrasound phase-change nanoemulsions assessed via high-speed optical microscopy," Physics in Medicine and Biology, vol. 58, p. 4513 (2013).
Sheeran et al., "Phase-change contrast agents for imaging and therapy," Curr. Pharm. Des., vol. 18, pp. 2152-2165 (2012).
Sheeran et al., "Design of Ultrasonically-Activatable Nanoparticles using Low Boiling Point Perfluorocarbons," Biomaterials, vol. 33, No. 11, pp. 1-21 (Apr. 2012).
Sheeran et al., "Formulation and Acoustic Studies of a New Phase-Shift Agent for Diagnostic and Therapeutic Ultrasound," Langmuir, vol. 27, No. 17, pp. 1-23 (Sep. 6, 2011).
Sheeran et al., "Decafluorobutane as a Phase-Change Contrast Agent for Low-Energy Extravascular Ultrasonic Imaging," Ultrasound in Medicine and Biology, vol. 37, No. 9, pp. 1518-1530 (2011).
Shortencarier et al., "A Method for Radiation-Force Localized Drug Delivery Using Gas-Filled Liposheres", IEEE Transactions on Ultrasonics, Ferroelectrics and Frequency Control, vol. 51, No. 7, pp. 822-831 (Jul. 2004).
Shpak et al., "Ultrafast dynamics of the acoustic vaporization of phase-change microdroplets," Journal of the Acoustical Society of America, vol. 134, pp. 1610-1621 (2013a).
Shpak et al., "The role of gas in ultrasonically driven bapor bubble growth," Physics in Medicine and Biology, vol. 58, pp. 2523-2535 (2013b).
Sirsi et al., "Microbubble Compositions, Properties and Biomedial Applications," Bubble Sci. Eng. Technol., vol. 1, pp. 1-28 (Nov. 2009).
Sittampalam et al., "High-Throughput Screening: Advances in Assay Technologies," Current Opinion in Chemical Biology, vol. 1(3), pp. 384-391 (1997).
Staub et al., "Contrast-Enhanced Ultrasound Imaging of the Vasa Vasorum: From Early Atherosclerosis to the Identification of Unstable Plaques," J. Am. Coll. Cardiol. Img., vol. 3, No. 7, pp. 761-771 (Jul. 2010).
Stephens et al., "Efficient Array Design for Sonotherapy," Phys Med Biol., vol. 53, No. 14, pp. 1-42 (Jul. 21, 2008).
Stephens et al., "Multi-frequency Array Development for Drug Delivery Therapies: Characterization and First Use of a Triple Row Ultrasound Probe," IEEE Ultrasonics Symposium, pp. 66-69 (2006).

(56) References Cited

OTHER PUBLICATIONS

Stieger et al., "Imaging of Angiogenesis Using Cadence Contrast Pulse Sequencing and Targeted Contrast Agents," Contrast Media & Molecular Imaging, vol. 3(1), pp. 9-18 (2008).
Stieger et al., "Enhancement of Vasular Permeability with Low-Frequency Contrast-Enhanced Ultrasound in the Chorioallantoic Membrane Model," Radiology, vol. 243, No. 1, pp. 112-121 (Apr. 2007).
Streeter et al., "Improving Sensitivity in Ultrasound Molecular Imaging by Tailoring Contrast Agent Size Distribution: In Vivo Studies," Molecular Imaging, vol. 9, No. 2, pp. 1-18 (Apr. 2010).
Stride et al., "Cavitation and Contrast: The Use of Bubbles in Ultrasound Imaging and Therapy," Proceedings of the Institution of Mechanical Engineers, Part H: Journal of Engineering in Medicine, vol. 224, pp. 171-191 (2010).
Strohm et al., "Vaporization of perfluorocarbon droplets using optical irradiation," Biomed. Opt. Express, vol. 2, pp. 1432-1442 (2011).
Takeuchi et al., "Enhanced Visualization of Intravascular and Left Atrial Appendage Thrombus with the USe of a Thrombus-Targeting Ultrasonographic Contrast Agent (MRX-408A1): In Vivo Experimental Echocardioraphic Studies," Journal of the American Society of Echocardiography, vol. 12, No. 12, pp. 1015-1021 (Dec. 1999).
Talu et al., "Needle Size and Injection Rate Impact Microbubble Contrast Agent Population," Ultrasound in Medicine & Biology, vol. 34, No. 7, pp. 1-8 (Jul. 2008).
Talu et al., "Maintaining Monodispersity in a Microbubble Population Formed by Flow-Focusing," Langmuir, vol. 24, No. 5, pp. 1-14 (Mar. 2008).
Talu et al., "Tailoring the Size Distribution of Ultrasound Contrast Agents: Possible Method for Improving Sensitivity in Molecular Imaging," Molecular Imaging, vol. 6, No. 6, pp. 1-19 (2007).
Talu et al., "Long-Term Stability by Lipid Coating Monodisperse Microbubbles Formed by a Flow-Focusing Device," Langmuir, vol. 22, No. 23, pp. 1-10 (Nov. 7, 2006).
Tan et al., "Microfluidic Separation of Satellite Droplets as the Basis of a Monodispersed Micron and Submicron Emulsification System," Lab Chip, vol. 5, pp. 1178-1183 (2005).
Tan et al., "Design of Microfludic Channel Geometries for the Control of Droplet Volume, Chemical Concentration, and Sorting," Lab Chip, vol. 4, pp. 292-298 (2004).
Tartis et al., "Therapeutic Effects of Paclitaxel-Containing Ultrasound Contrast Agents," Ultrasound in Medicine and Biology, vol. 32, No. 11, pp. 1771-1780 (2006).
Teh et al., "Droplet Microfluidics," Lab Chip, vol. 8, pp. 198-220 (2008).
Ten Kate et al., "Molecular Imaging of Inflammation and Intraplaque Vasa Vasorum: A Step Forward to Identification of Vulnerable Plaques?," Journal of Nuclear Cardiology, vol. 17, pp. 897-912 (2010).
Teytelman et al., "Impact of Chromatin Structures on DNA Processing for Genomic Analyses," PLoS ONE, vol. 4, Issue 8, e6700, pp. 1-11 (Aug. 2009).
Thorstenson et al., "An Automated Hydrodynamic Process for Controlled, Unbiased DNA Shearing," Genome Research, vol. 8, pp. 848-855 (Aug. 1998).
Tinkov et al., "Microbubbles as Ultrasound Triggered Drug Carriers," Journal of Pharmaceutical Sciences, vol. 98, No. 6, pp. 1935-1961 (2009).
Torchilin, "Passive and Active Drug Targeting: Drug Delivery to Tumors as an Example," Handbook of Experimental Pharmacology, pp. 3-53 (2010).
Tortoli et al., "Unexpected Doppler Effects from Microbubbles Moving Through an Ultrasound Beam," IEEE Ultrasonics Symposium, vol. 2, pp. 1729-1732 (1999).
Ueda et al., "Acoustic Cavitation as an Enhancing Mechanism of Low-Frequency Sonophoresis for Transdermal Drug Delivery," Biol. Pharm. Bull, vol. 32, No. 5, pp. 916-920 (2009).
Unger et al., "Therapeutic Applications of Lipid-Coated Microbubbles," Advanced Drug Delivery Reviews, vol. 56, pp. 1291-1314 (2004).
Unger et al., "Therapeutic Applications of Microbubbles," European Journal of Radiology, vol. 42, pp. 160-688 (2002).
Unger et al., "Local Drug and Gene Delivery Through Microbubbles," Progress in Cardiovascular Diseases, vol. 44, No. 1, pp. 45-54 (Jul./Aug. 2001).
Unger et al., "In Vitro Studies of a New Thrombus-Specific Ultrasound Contrast Agent," Am J Cardiol, vol. 81, No. 12A, pp. 58G-61G (1998).
Van Wamel et al., "Vibrating Microbubbles Poking Individual Cells: Drug Transfer Into Cells Via Sonoporation," Journal of Controlled Release, vol. 112, pp. 149-155 (2006).
Villanueva, "Molecular Imaging of Cardiovascular Disease Using Ultrasound," J. Nucl. Cardiol., vol. 15, No. 4, pp. 1-18 (2008).
Villanueva et al., "Microbubbles Targeted to Intracellular Adhesion Molecule-1 Bind to Activated Coronary Artery Endothelial Cells," Circulation, vol. 98, pp. 1-6 (1998).
Vorkurka, "Comparison of Rayleigh's, Herring's, and Gilmore Models of Gas Bubbles," Acustica, vol. 59, pp. 214-219 (1986).
Wang et al., "Controllable Microfludic Production of Multicomponent Multiple Emulsions," Lab Chip, vol. 11, pp. 1587-1592 (Mar. 9, 2011).
Ward et al., "Experimental Study of the Effects of Optison Concentration on Sonoporation In Vitro," Ultrasound in Medicine & Biology, vol. 26, No. 7, pp. 1169-1175 (May 2, 2000).
Watanabe et al., "Translational and Radical Motions of a Bubble in an Acoustic Standing Wave Field," Phys. Fluids A, vol. 5, No. 11, pp. 2682-2688 (Nov. 1993).
Wei et al., "Recent Advances in Myocardial Contrast Echoardiography," Curr. Opin. Cardiol., vol. 12, pp. 539-546 (1997).
Whittingham, "Contrast-specific imaging techniques: technical perspective," Contrast Media in Ultrasonography: Basic Principles and Clinical Applications, pp. 43-70 (2005).
Whitworth, "Discussion of One-D Piezoelectric Transducer Models With Loss," IEEE Transactions on Ultrasonics, Ferroelectrics and Frequency Control, vol. 48, No. 3, pp. 844-846 (May 2001).
Wigle et al., "Screening for Inhibitors of Low-Affinity Epigenetic Peptide-Protein Interactions: An AlphaScreen™—Based Assay for Antagonists of Methyl-Lysine Binding Proteins," Journal of Biomolecular Screening, vol. 15, No. 1, pp. 62-71 (2010).
Wilson et al., "Biomedical photoacoustics beyond thermal expansion using triggered nanodroplet vaporization for contrast-enhanced imaging," Nature Communications, vol. 3, p. 618 (2012).
Wilson et al., "Microbubble-Enhanced US in Body Imaging: What Role?," Radiology, vol. 257, No. 1, pp. 24-39 (Oct. 2010).
Wong et al., "Bubble Evolution in Acoustic Droplet Vaporization at Physiological Temperature via Ultra-high Speed Imaging," Soft Matter, vol. 7, pp. 4009-4016 (Jan. 2011).
Wong et al., "A Novel Method for Producing Partial Restriction Digestion of DNA Fragments by PCR with 5-methyl-CTP," Nucleic Acids Research, vol. 25, No. 20, pp. 4169-4171 (1997).
Wright et al., "Evaluation of New Thrombus-Specific Ultrasound Contrast Agent," Acad Radiol, vol. 5 (supp 1), pp. S240-S242 (1998).
Wu et al., "PSPICE Approach for Designing the Ultrasonic Piezoelectric Transducer for Medical Diagnostic Applications," Sensors and Actuators, vol. 75, pp. 186-198 (1999).
Xu et al., "Controllable Preparation of Monodisperse O/W and W/O Emulsions in the Same Microfluidic Device," Langmuir, vol. 22, No. 19, pp. 7943-7946 (Sep. 12, 2006).
Xu et al., "Generation of Monodisperse Particles by Using Microfluidics: Control Over Size, Shape, and Composition," Angew. Chem. Int. Ed., vol. 44, pp. 724-728 (2005).
Yasuda et al., "Using Acoustic Radiation Force as a Concentration Method for Erythrocytes," J. Acoust. Soc. Am., vol. 102, No. 1, pp. 642-645 (Jul. 1997).
Ye et al., "Microbubble Expansion in a Flexible Tube," Transactions of the ASME, vol. 128, pp. 554-563 (Aug. 2006).
Ye et al., "Direct Numerical Simulations of Micro-Bubble Expansion in Gas Embolotherapy," Journal of Biomedical Engineering, vol. 126, pp. 745-759 (Dec. 2004).
Zhang et al., "Acoustic Droplet Vaporization for Enhancement of Thermal Ablation by High Intensity Focused Ultrasound," Acad Radiol., vol. 18, No. 9, pp. 1-20 (Sep. 2011).

(56) References Cited

OTHER PUBLICATIONS

Zhang et al., "Initial Investigation of Acoustic Droplet Vaporization for Occulsion in Canine Kidney," Ultrasound Med Biol., vol. 36, No. 10, pp. 1-33 (Oct. 2010).
Zhang et al., "An in Vitro Study of a Phase-Shift Nanoemulsion: A Potential Nucleation Agent for Bubble-Enhanced HIFU Tumor Ablation," Ultrasound in Med. & Biol., vol. 36, No. 11, pp. 1856-1866 (2010).
Zhao et al., "Selective Imaging of Adherent Targeted Ultrasound Contrast Agents," Physics in Medicine and Biology, vol. 52, pp. 2055-2072 (2007).
Zhao et al., "Radiation-Force Assisted Targeting Facilitates Ultrasonic Molecular Imaging," Molecular Imaging, vol. 3, No. 3, pp. 135-148 (Jul. 2004).
Zheng et al., "A Novel Sensitive Targeted Imaging Technique for Ultrasonic Molecular Imaging," IEEE 2007 Ultrasonics Symposium, pp. 957-960 (2007).
Zheng et al., "Ultrasound-Driven Microbubble Oscillation and Translation Within Small Phantom Vessels," Ultrasound in Med. & Biol., vol. 33, No. 12, pp. 1978-1987 (2007).
Zhou et al., "The Size of Sonoporation Pores on the Cell Membrane," Ultrasound in Medicine & Biology, vol. 35, No. 10, pp. 1-10 (Oct. 2009).
Zipparo, "Mid- to High-Power Ultrasound Imaging Arrays—from ARFI to HIFU," IEEE 2003 Ultrasonics Symposium; Honolulu, Hawaii, pp. 684-688 (2003).
Fuciarelli et al., "Induction of Base Damage in DNA Solutions by Ultrasonic Cavitation," Free Radical Biology & Medicine, vol. 18, No. 2, pp. 231-238 (1995).
Advisory Action, Examiner-Initiated Interview Summary and AFCP 2.0 Decision for U.S. Appl. No. 15/035,211 (dated Mar. 7, 2019).
Non-Final Office Action for U.S. Appl. No. 15/247,840 (dated Oct. 5, 2018).
Final Office Action for U.S. Appl. No. 15/035,211 (dated Sep. 26, 2018).
Joneja et al., "A device for automated hydrodynamic shearing of genomic DNA," Biotechniques, vol. 46, pp. 1-7 (2009).
Dayton et al., "Application of Ultrasound to Selectively Localize Nanodroplets for Targeted Imaging and Therapy," Molecular Imaging, vol. 5, No. 3, pp. 1-32 (2006).
Janzen et al., "Advances in improving the quality and flexibility of compound management," Journal of Biomolecular Screening, vol. 14, No. 5, pp. 444-451 (2009).
Janzen et al., "A Chemogenonic Approach to Discovering Target Selective Drugs," Chemical Biology and Drug Design, vol. 67, Issue 1, pp. 85-86 (2006).
Kogan et al., "Microbubbles in Imaging: Application Beyond Ultrasound," In Bubble Science, Engineering, and Technology, vol. 2, No. 1, pp. 1-11 (Jun. 2010).
Lipinski, "Lead- and Drug-like compounds: the rule-of-five revolution," Drug Discovery Today, vol. 1, pp. 337-341 (2004).
Liu et al., "Protein Lysine Methyltransferase G9a Inhibitors: Design, Synthesis, and Structure Activity Relationships of 2,4-Diamino-7-aminoalkoxy-quinazolines," J. Med. Chem., vol. 53, PMCID: PMC2920043, NIHMSID: NIHMS220759, pp. 5844-5857 (2011).
Macarron et al., "Impact of high-throughput screening in biomedical research," Nature Reviews Drug Discovery, vol. 10, pp. 188-195 (2011).
Marvel et al., "The Development and Validation of a LIPUS System with Preliminary Observations of Ultrasonic Effects on Human Adult Stem Cells," IEEE Transactions on Ultrasonics, Ferroelectrics, and Frequency Control, vol. 57, No. 9, pp. 1977-1984 (Sep. 2010).
Marvel et al., "Application of Low Intensity Pulsed Ultrasound for Functional Bone Tissue Engineering using Adult Stem Cells," IEEE International Ultrasonics Symposium Proceedings, pp. 357-360 (2009).
Sittampalam et al., "Design of Signal Windows in High Throughput Screening Assays for Drug Discovery," Journal of Biomolecular Screening, vol. 2, No. 3, pp. 159-169 (1997).
Vedadi et al., "A chemical probe selectively inhibits G9a and GLP methyltransferase activity in cells," Nature Chemical Biology, vol. 7, No. 8, pp. 1-21 (Jul. 10, 2011).
Walters et al., "Prediction of 'drug-likeness'", Advanced Drug Delivery Reviews, vol. 54, pp. 255-271 (2002).
Wigle et al., "Accessing Protein Methyltransferase and Demethylase Enzymology Using Microfluidic Capillary Electrophoresis," Chem Biol., vol. 17, No. 7, pp. 1-19 (2010).
Zhao et al., "Acoustic response from adherent targeted contrast agents," Journal of the Acoustical Society of America, vol. 120, No. 6, pp. 1-11 (2006).

* cited by examiner

600 — INTRODUCE PARTICLES CONTAINING STABLE, ACTIVATABLE NANODROPLETS, EACH NANODROPLET INCLUDING A LIQUID ENCAPSULATED IN A SHELL, WHERE THE LIQUID COMPRISES AT LEAST ONE COMPONENT THAT IS A GAS AT ROOM TEMPERATURE AND ATMOSPHERIC PRESSURE, INTO A BLOOD VESSEL IN THE VICINITY OF A TARGET REGION

602 — WAIT UNTIL A SUFFICIENT NUMBER OF PARTICLES EXTRAVASATE INTO THE TARGET REGION

FIG. 6

FORMULATION OF ACOUSTICALLY ACTIVATABLE PARTICLES HAVING LOW VAPORIZATION ENERGY AND METHODS FOR USING SAME

PRIORITY CLAIM

This application is a divisional of U.S. patent application Ser. No. 15/247,840 filed Aug. 25, 2016, which is a divisional of U.S. patent application Ser. No. 13/876,165, for which the national stage was entered on Mar. 26, 2013 and was given a 35 U.S.C. § 371(c) date of Aug. 30, 2013 (now U.S. Pat. No. 9,427,410), which is a national stage application under 35 U.S.C. § 371 of PCT Patent Application No. PCT/US2011/055713 filed Oct. 11, 2011, which claims the benefit of U.S. Provisional Patent Application Ser. No. 61/391,569, filed Oct. 8, 2010; and which claims the benefit of U.S. Provisional Patent Application Ser. No. 61/505,915 filed, Jul. 8, 2011; the disclosures of which are incorporated herein by reference in their entireties.

Glossary of Terms

The following is a glossary of abbreviations used herein:
ADV acoustic droplet vaporization
DDFP dodecafluoropentane (also known as PFP)
DPPC dipalmitoylphosphatidylcholine
DPPE-PEG 1,2-dipalmitoyl-sn-glycero-3-phosphoethanolamine-N-[methoxy(polyethylene glycol)-2000]
DFB decafluorobutane (also known as PFB)
DSPC distearoyl phosphocholine
EPR enhanced permeability and retention
FDA United States Food and Drug Administration
HEPES (4-2-hydroxyethyl)piperazine-1-ethanesulfonic acid
LPC palmitoyl-2-hydroxy-sn-glycero-3-phosphocholine
MCA micro-bubble contrast agents
OFP octafluoropropane
PBS phosphate-buffered saline
PCA phase-change agent
PCCA phase-change contrast agent
PEG polyethylene glycol
PFC perfluorocarbon/perfluorochemical—(includes PFB, PFP, PFMP, and OFP)
PFB perfluorobutane (also known as DFB)
PFH perfluorohexane
PFMP perfluoro(2-methyl-3-pentanone)
PFP perfluoropentane (also known as DDFP)
TAPS trimethylamino propane

GOVERNMENT INTEREST

This invention was made with government support under Grant No. EB011704 awarded by the National Institutes of Health. The government has certain rights in the invention.

BACKGROUND

The term "bubble" as used herein refers to a bubble of gas encased or surrounded by an enclosing substance. Bubbles that are from one micrometer to several tens or hundreds of micrometers in size are commonly referred to as "microbubbles", while bubbles that are smaller than one micrometer in size are commonly referred to as "nanobubbles." The term "droplet" as used herein refers to an amount of liquid that is encased or surrounded by a different, enclosing substance. Droplets that are less than one micrometer in size are commonly referred to as "nanodroplets" and those that are in the one micrometer to tens or hundreds of micrometers in size are commonly referred to as "microdroplets." If a droplet is encased in another liquid, the droplet and its casing may also be referred to as an "emulsion". The term "particle" as used herein refers to either a droplet or a bubble of any size.

Microbubbles for diagnostic ultrasound imaging have been established in the clinical arena as a sensitive and inexpensive imaging technique for interrogating landmarks in the vasculature. Currently, microbubble-enhanced diagnostic ultrasound has been approved by the FDA for the study of wall motion abnormalities and ventricular contraction in echocardiography. Researchers have proposed microbubble-aided ultrasound for a wide range of potential applications, including functional tumor, kidney, and liver imaging, identification of vascular inflammation, identification of vulnerable plaque deposition, thrombus detection and targeted molecular imaging of angiogenesis. Microbubbles have been used for therapeutic interventions, primarily in concert with ultrasound-mediated cavitation for sonothrombolysis.

Despite their utility as vascular contrast agents and potential for therapeutic applications, microbubble size (typically 1-5 microns in diameter) prevents their transport outside of the vasculature, a process commonly referred to as extravasation. In other words, microbubbles are trapped within the circulatory system. In order to extravasate into the interstitial space in a solid tumor, the bubble would need to be smaller than a micron, i.e., a nanoparticle is required. The exact size limit for nanoparticle extravasation into the interstitial space in solid tumors depends on a variety of factors, but has been reported to fall within the range of 100 nm-750 nm.

Nanoparticles make poor ultrasound contrast agents, however. Nanobubbles small enough to diffuse past inter-endothelial gap junctions scatter ultrasound energy poorly compared to microbubbles and thus provide limited imaging contrast. Additionally, bubble circulation in vivo is shown to be on the order of tens of minutes before bubble dissolution, and clearance significantly limits contrast enhancement. This short time period may be insufficient for enough bubbles to accumulate by diffusion into the tumor interstitium. Droplets of any size provide poor contrast for ultrasound imaging as compared to equivalently sized bubbles, and nanodroplets small enough to extravasate into the interstitial space in solid tumors provide poorer contrast still.

One approach to solve the problem of providing ultrasound contrast agents that are both small enough to extravasate and large enough to provide sufficient ultrasound contrast has been to produce a droplet that is small enough to extravasate but which can be caused to expand into a bubble, a processed referred to as "activation". Such particles are commonly referred to as "phase change agents". One method of activation is known as acoustic droplet vaporization, or ADV. In ADV, the droplet is subjected to ultrasonic energy, which causes the liquid within the droplet to change phase and become a gas. This causes the droplet to become a bubble, with the corresponding increase in size. The ultrasound impulses impart a mechanical pressure upon the tissues, and the amount of pressure applied is indicated in terms of a mechanical index, or MI.

Particles that start as droplets but can be activated to become bubbles are referred to as "metastable", because they are stable as droplets (e.g., they don't spontaneously expand into bubbles) without additional energy. If these PCAs are used as contrast agents, they are commonly referred to as "phase-change contrast agents" (PCCAs).

Recently there has been interest in the use of PFC droplets for this purpose. To date, PCAs have been developed using PFCs which have boiling points above room temperature (25° C.), which are herein referred to as "low volatility PFCs". Examples include dodecafluoropentane (DDFP), perfluorohexane (PFH), and perfluoroheptane. These low volatility PFCs have been used to make PCAs that have a diameter greater than 1 micron, i.e., microdroplets or microbubbles. PFCs with boiling points above room temperature, which are herein referred to as "high volatility" or "highly volatile" PFCs, have not been used to make microparticles out of a concern that, if subjected to body temperature (37° C.), a droplet containing a highly volatile PFC might spontaneously change phase.

However, the low-volatility PFCs conventionally used to make micro-PCAs are not suitable for making nano-PCAs. Many in vitro studies have shown that the energy required to activate a PFC-based PCA increases as the diameter of the initial droplet decreases. There is a direct correlation between activation energy and mechanical index, and applications involving relatively low frequencies and/or sub-micron droplets may require pressures higher than diagnostic ultrasound machines currently provide. This is an obstacle to human treatment, because excessive ultrasonic activation energy can cause tissue damage or other unwanted bioeffects.

Thus, PFCs that had been used in microbubbles may be unsuitable for use in nanodroplets due to the excessive activation energy required. The smaller the nanodroplet, the more activation energy is required, and the less suitable the PFC. For example, the Antoine vapor pressure equation was analyzed in order to assess the theoretical vaporization temperature dependence upon droplet diameter of selected PFCs as a result of the influence of interfacial surface tension. Using this model to investigate the influence of PFC boiling points, it was concluded that DDFP, PFH, and perfluoroheptane may require a relatively large amount of energy in order to elicit droplet vaporization at a size that would practically be able to extravasate through endothelial gap junctions and into the extravascular space.

Therefore, there exists a need for a phase-change agent that is stable at physiological temperatures yet is more susceptible to ultrasound pressures. Such a particle could provide a more efficacious vehicle for extravasation into tissue and activation at the site of action in many applications. For human therapeutic and diagnostic use, there is a need for a stable nanoparticle capable of being vaporized using frequencies and mechanical indices within the FDA-approved limits of commercial clinical diagnostic ultrasound machines.

SUMMARY

The subject matter described herein includes formulation methods and applications for particles that can be activated by acoustic energy to convert from a liquid state to a gas state. In one embodiment, nanoparticles suitable for use in human diagnostics, imaging, therapeutics, and treatment are presented. The methods described herein produce stabilized nano- and micro-particles, in liquid or emulsion form, of compounds that are normally gas at room temperature and atmospheric pressure. Two distinct methods are disclosed: the first is called the "droplet extrusion" method and the second is called the "bubble condensation" method.

In one embodiment, the droplet extrusion method includes causing the first substance to condense into a liquid and then extruding or emulsifying the first substance into or in the presence of a second substance to create droplets or emulsions in which the first substance is encapsulated by the second substance. To condense the first substance, it may be cooled to a temperature below the phase transition temperature of the component having the lowest boiling point, it may be compressed to a pressure above the phase transition pressure of the component having the highest phase transition pressure value, or a combination of the above. The contents of the droplet or emulsion so formed may be entirely or primarily in a liquid phase.

In one embodiment, the bubble condensation method includes extruding or emulsifying the first substance into or in the presence of the second substance to create bubbles having an outer shell of the second substance encapsulating an amount of the first substance, at least some of which is in gaseous form. The bubble thus formed is cooled and/or compressed such that the contents of the bubble reach a temperature below the phase transition temperature of the component having the lowest boiling point at that pressure. This causes the gas within the bubble to condense to a liquid phase, which transforms the bubble into a droplet or emulsion. In this manner, droplets or emulsions in which the first substance is encapsulated by the second substance are created.

The two methods described above produce particles containing in liquid form a substance that is normally a gas at room temperature and pressure, and stabilizing these particles in their liquid form using a shell such as a lipid, protein, polymer, gel, surfactant, or sugar. The surface tension of the shell enables these particles to be stable in liquid form, even when the surrounding temperature is raised back to room temperature. Acoustic energy can then "activate" the particle, returning it to gas form.

In one embodiment, a method for delivery of particles to a target region includes introducing particles comprising stable, activatable nanodroplets, each nanodroplet comprising a liquid encapsulated in a shell, where the liquid comprises at least one component that is a gas at room temperature and atmospheric pressure, into a blood vessel in the vicinity of a target region. The particles then extravasate into the target region.

In one embodiment, a method for medical diagnostic imaging using activatable droplets as contrast agents includes producing encapsulated droplets, each encapsulated droplet containing a liquid encapsulated in a shell, where the liquid includes a liquid phase of a fluorocarbon, a perfluorocarbon, a chlorofluorocarbon, a hydrofluorocarbon, a hydrocarbon, a gas having a boiling point that is below room temperature (25° C.), or combinations thereof; introducing the encapsulated droplets into a tissue to be imaged; providing activation energy sufficient to cause the liquid within the encapsulated droplets to change from a liquid phase to a gas phase, causing the encapsulated droplets to increase in size and become bubbles of encapsulated gas; and performing ultrasonic imaging of the tissue using the bubbles as a contrast agent.

In one embodiment, a method for medical therapy using activatable droplets includes producing encapsulated droplets, each encapsulated droplet including a liquid encapsulated in a shell, where the liquid comprises a liquid phase of a fluorocarbon, a perfluorocarbon, a chlorofluorocarbon, a hydrofluorocarbon, a hydrocarbon, a gas having a boiling point that is below room temperature (25° C.), or combinations thereof; including a therapeutic agent in or on the shell; delivering the encapsulated droplets to a target region; and providing activation energy sufficient to cause the liquid within the encapsulated droplets to change from a liquid phase to a gas phase, causing the encapsulated droplets to increase in size and become bubbles of encapsulated gas, wherein the substance to be delivered to the target tissue enters into the cells of the target tissue.

In one embodiment, a method for medical therapy using activatable droplets includes producing encapsulated droplets, each encapsulated droplet including a liquid encapsulated in a shell, where the liquid includes a liquid phase of a fluorocarbon, a perfluorocarbon, a chlorofluorocarbon, a hydrofluorocarbon, a hydrocarbon, a gas having a boiling point that is below room temperature (25° C.), or combinations thereof; delivering the encapsulated droplets to a target tissue; and providing activation energy sufficient to cause the liquid within the encapsulated droplets to change from a liquid phase to a gas phase, causing the encapsulated droplets to increase in size and become bubbles of encapsulated gas, where the bubbles obstruct the flow of blood, oxygen, or nutrients to a target region.

In one embodiment, a method of size selection of particles including droplets or emulsions having at least one component that is a gas at room temperature and atmospheric pressure encapsulated in liquid form inside a lipid, protein, or polymer capsule, includes exposing the particles to at least one of a pressure other than atmospheric pressure and a temperature other than room temperature, thereby causing some portion of the particle distribution to become activated, and separating the activated particles from the non-activated particles.

Acoustically activatable particles having low vaporization energy and methods for making and using same are disclosed. A particle of material includes a first substance that includes at least one component that is a gas 25° C. and atmospheric pressure. A second substance, different from the first substance, encapsulates the first substance to create a droplet or emulsion that is stable at room temperature and atmospheric pressure. At least some of the first substance exists in a gaseous phase at the time of encapsulation of the first substance within the second substance to form a bubble. After formation of the bubble, the bubble is condensed into a liquid phase, which causes the bubble to transform into the droplet or emulsion having a core consisting of a liquid. The droplet or emulsion is an activatable phase change agent that remains a droplet having a core consisting of a liquid at 25° C. and atmospheric pressure. The first substance has a boiling point below 25° C. at atmospheric pressure.

BRIEF DESCRIPTION OF THE DRAWINGS

Preferred embodiments of the subject matter described herein will now be explained with reference to the accompanying drawings, wherein like reference numerals represent like parts, of which:

FIG. 1 is a graph illustrating the relationship between droplet diameter, shown on the X-axis, and predicted vaporization temperature, shown on the Y-axis, for lipid-encapsulated nanodroplets, each containing one of four common PFCs;

FIG. 2 is a flow chart illustrating an exemplary process for preparing particles of materials having a first substance that is enclosed by second substance that acts as an encapsulating material, where the first substance includes at least one component that is a gas at room temperature and atmospheric pressure, according to an embodiment of the subject matter described herein;

FIG. 3 is a flow chart illustrating an exemplary process for preparing particles of materials having a first substance that is enclosed by second substance that acts as an encapsulating material, where the first substance includes at least one component that is a gas at room temperature and atmospheric pressure, according to another embodiment of the subject matter described herein;

FIG. 4 is a graph showing an observed relationship between initial diameter of a droplet generated according to methods described herein and the mechanical index required to vaporize it;

FIG. 5 is a graph illustrating activation energy for droplets containing DFB, droplets containing OFP, and droplets containing a 50%/50% mix of DFB and OFP, generated using the bubble condensation method according to an embodiment of the subject matter described herein;

FIG. 6 is a flow chart illustrating an exemplary process for delivery of particles to a target region according to an embodiment of the subject matter described herein;

FIG. 7 is a flow chart illustrating an exemplary process for medical diagnostic imaging using activatable droplets as contrast agents according to an embodiment of the subject matter described herein;

FIG. 8 is a flow chart illustrating an exemplary process for medical therapy using activatable droplets as a vehicle for delivering therapeutic agents according to an embodiment described herein;

FIG. 9 is a flow chart illustrating an exemplary process for medical therapy using activatable droplets to obstruct the flow of blood, oxygen, or nutrients to cells, such as tumor tissues, according to an embodiment of the subject matter described herein; and FIG. 10 is a flow chart illustrating an exemplary process for size selection of particles according to an embodiment described herein.

DETAILED DESCRIPTION

An ideal phase change agent for use where extravasation into interstitial regions of tissue is desired, such as an extravascular ultrasound contrast agent, for applications where thermal and cavitation-based bioeffects are minimized should be: 1) stable in the vasculature for a sufficient time period, 2) capable of extravasation out of the vascular space, and: 3) labile enough to be activated and interrogated by clinical ultrasound machines at clinically relevant acoustic intensities. The subject matter described herein includes methods to produce acoustically activatable nanoparticles that are formulated with high volatility PFCs yet remain stable at room temperature and pressure. The resulting droplets are acoustically activatable with substantially less energy than other favored compounds proposed for phase-change contrast agents. Also presented are uses of these nanoparticles in medical diagnostics, imaging, therapy, and treatment. In one embodiment, the activation energy of the nanoparticle may be tuned to a particular value, opening up the possibility of highly-targeted treatments.

To determine which PFCs had potential as a phase-change contrast agent at physiological temperatures and with pre-activation droplet size in the range desired for extravasation, it was necessary to estimate the energy that would be required to activate droplets containing the PFCs. The energy required depends on both the PFC contained within the droplet and the diameter of the droplet itself. To estimate this energy, calculations were performed using the Antoine vapor-pressure equation. This equation was derived from the Clausius-Clapeyron relation by Antoine in 1888, and when re-arranged for temperature is expressed as:

$$T = \frac{B}{A - \log_{10} P} - C \quad \text{(Eq. #1)}$$

where P is pressure, T is temperature, and A, B, and C are gas-dependent constants observed to be valid for a particular temperature range. This equation uses experimental results to develop a basic relationship between temperature and pressure as a droplet of a particular substance vaporizes. A droplet will experience an additional pressure due to interfacial surface tension effects, defined as the Laplace pressure:

$$\Delta P = P_{inside} - P_{outside} = \frac{2\sigma}{r} \quad \text{(Eq. #2)}$$

where r is the radius of the droplet, $\sigma$ is surface tension, and $P_{inside}$ and $P_{outside}$ represent the pressure inside the droplet core and the ambient pressure in the surrounding media, respectively. PFCs typically have fairly low surface tension values on the order of 10 mN/m at room temperature.

Because the Laplace pressure is an inverse function of radius, smaller droplets will experience greater pressure. Encapsulating the droplets in a lipid or polymer shell stabilizes the droplets from coalescence and alters the interfacial surface tension. Depending on the properties of the encapsulating shell, a larger resulting surface tension may cause an increase in the pressure exerted, which essentially increases the vaporization temperature of the droplet.

In designing agents for human medical imaging purposes, the ambient pressure may be defined as:

$$P_{amb} = P_{atm} + P_{body} \quad \text{(Eq. #3)}$$

where $P_{atm}$=101.325 kPa and $P_{body}$ is a representative pressure inside the human body (vascular or other). Although intravascular pressure is inherently pulsatile, for the purposes of these calculations, an average value of $P_{body}$=12.67 kPa was used. With a total pressure exerted on the droplet of:

$$P = P_{amb} + \Delta P = P_{atm} + P_{body} + \frac{2\sigma}{r} \quad \text{(Eq. #4)}$$

the resulting modified Antoine vapor-pressure equation is:

$$T = \frac{B}{A - \log_{10}\left(P_{atm} + P_{body} + \frac{2\sigma}{r}\right)} - C \quad \text{(Eq. #5)}$$

Published surface tensions often vary between 25 mN/m and 50-60 mN/m, depending on surfactant properties. Although the exact surface tension of lipid solutions used in published studies was not known, a value near 51 mN/m was sufficient for the purposes of these initial calculations in that it provided a Laplace pressure near the upper limit of what can be expected. The constants A,B,C were gathered from the National Institute of Standards and Technology (NIST) Chemistry WebBook (Linstrom and Mallard 2010) for the nearest available temperature range. The results of these calculations is shown in FIG. 1.

FIG. 1 is a graph illustrating the relationship between droplet diameter, shown on the X-axis, and predicted vaporization temperature, shown on the Y-axis, for lipid-encapsulated nanodroplets, each containing one of four common PFCs: perfluorohexane (PFH), dodecafluoropentane (DDFP), decafluorobutane (DFB), and octafluoropropane (OFP), shown with human body temperature for comparison. The natural boiling points of PFH, DDFP, DFB, and OFP are 56.6° C., 29° C., −1.7°, and −37.6° C., respectively.

In order to estimate the size of the bubble produced by activating a droplet, ideal gas laws (PV=nRT, where n, P, V, and T represent the number of moles of PFC, pressure, volume, and temperature, respectively) can be used to approximate the expansion factor when a liquid undergoes a phase conversion to the gaseous state. Because perfluorocarbons are immiscible in the liquid state and have low diffusivity in the gaseous state, here it is assumed that the number of moles is constant from the liquid phase to the gaseous phase ($n_l$=$n_g$). The moles of PFC in the spherical droplet can be computed as:

$$n_l = \frac{4\pi r_l^3 \rho_l}{3M} \quad \text{(Eq. #6)}$$

where $r_l$ is the radius of the liquid droplet, $\rho_l$ is the liquid density, and M is the molar mass. Substituting this into the ideal gas law and simplifying as a ratio of the gas-phase radius to liquid-phase radius gives:

$$\frac{r_g}{r_l} = \sqrt[3]{\frac{\rho_l RT}{MP}} \quad \text{(Eq. #7)}$$

Expanding with Eq. #4 gives $$\frac{r_g}{r_l} = \sqrt[3]{\frac{\rho_l RT}{M\left(P_{atm} + P_{body} + \frac{2\sigma}{r_g}\right)}} \quad \text{(Eq. #8)}$$

As $r_g$ approaches very large values, the surface tension component becomes negligible.

Decafluorobutane has a molar mass of M=0.238 kg/mol, and at 37° C. (310 K) $\rho_l \approx$1500 kg/m$^3$. Evaluating Eq. #8 with in vivo ($P_{body}$=12.67 kPa) and in vitro ($P_{body}$=0 kPa) conditions and neglecting surface tension effects reveals that, based on the assumptions given, a droplet of DFB can be predicted to expand to an approximate upper limit of 5.2 to 5.4 times its original diameter once vaporized (neglecting any deviations from ideal gas laws). Rearranging Eq. #8 such that it is solved for liquid droplet radius becomes:

$$r_l = \sqrt[3]{\frac{Mr_g^2[r_g(P_{atm} + P_{body}) + 2\sigma]}{\rho_l RT}} \quad \text{(Eq. #9)}$$

This allows one, based on ideal gas laws and surface tension effects, to estimate the size of the droplet that vaporized to become a bubble of a known size. Eq. #8 can also be solved for $r_g$, providing a numerically equivalent—though much more complex—solution. For the purposes of this study, Eq. #9 becomes a more convenient solution, as measured bubble sizes are used to estimate originating droplet sizes.

While the constants used are not expected to predict the vaporization relationship completely accurately in the desired temperature range, the calculation shows DFB droplets appear to have the potential to remain stable in the 200-600 nm diameter range at temperatures just above body temperature and that the bubble created by activating the droplet will be of sufficient size to effectively perform as an ultrasound contrast agent. The calculation also shows that OFP droplets have the potential to remain stable at sizes below 200 nm, although the −37.6° C. boiling point presents significant generation challenges. However, no method to create DFB or OFP droplets in the sub-micron size range was known or found in the prior art.

The subject matter described herein includes two methods creating stable droplets or emulsions, including particles less than 1 micron in diameter, that contain PFCs with low boiling points, including PFCs with boiling points that are below body temperature (37° C.) or below room temperature (25° C.), by encapsulating the particles in a lipid, protein, polymer, gel, surfactant, peptide, or sugar. It has been shown that this technique may be used to successfully create stable nanodroplets containing DFP, OFP, or a mixture of the two, with and without other substances, where the substance being encapsulated would otherwise vaporize without the stabilizing encapsulation. The nanodroplets so created have activation energies that are low enough that the nanodroplets may be used for human diagnostics, therapeutics, and treatment. The subject matter described herein also includes methods of using these nanodroplets for diagnostics, therapeutics, and other treatments.

Droplet Extrusion Method.

Figure 2:
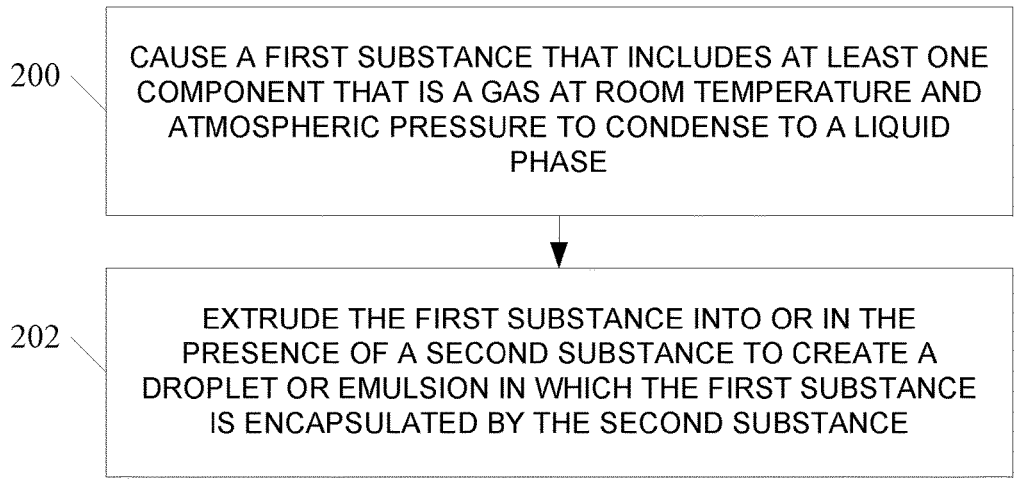

FIG. 2 is a flow chart illustrating an exemplary process for preparing particles of materials having a first substance that is enclosed by second substance that acts as an encapsulating material, where the first substance includes at least one component that is a gas at room temperature and atmospheric pressure, according to an embodiment of the subject matter described herein. Example particles include droplets or emulsions. The first substance may be herein referred to as, for example, "the encapsulated substance", "the contents", "the filler", "the filling", "the core", and the like. The second substance may be herein referred to as, for example, "the encapsulating substance", "the encapsulation material", "the capsule", "the container", "the shell", and the like.

At block 200, the first substance condensed to a liquid phase. This may be done, for example, by cooling the first substance to a temperature below the phase transition temperature of the component having the lowest boiling point, by compressing the first substance to a pressure that is above the phase transition pressure of the component having the highest phase transition pressure, or a combination of the above.

At block 202, the first substance is extruded into or in the presence of the second substance to create droplets or emulsions in which the first substance is encapsulated by the second substance. In one embodiment, the contents of the droplet or emulsion is entirely or primarily in a liquid phase.

In one embodiment the particles are extruded at a temperature below the phase transition temperature of the component having the lowest boiling point. In one embodiment, the particles are formed through a flow-focusing junction in a microfluidic device, where the device is maintained at a temperature below the phase transition temperature of the component having the lowest boiling point.

In one embodiment, the particles are extruded in a pressurized environment, where the ambient pressure is above phase transition pressure of the component having the highest phase transition pressure. In one embodiment, the particles are extruded at a temperature that is either above or below the boiling point of the component having the lowest boiling point. In one embodiment, the particles are extruded at a temperature that is below the boiling point of the component having the lowest boiling point.

In one embodiment, the preparation involves shaking. In one embodiment, the preparation involves extrusion through a filter. In one embodiment, the filter has a pore size greater than the size of the desired particle. In one embodiment, the pore size is 10 times greater than the desired particle size. In one embodiment, the pore size is 2-7 times greater than the desired particle size. In one embodiment, the pore size is 3-6 times greater than the desired particle size. In one embodiment, the pore size is 5 times greater than the desired particle size.

In one embodiment, the first substance being encapsulated includes a gas, such as a fluorocarbon, a perfluorocarbon, a chlorofluorocarbon, a hydrofluorocarbon, a hydrocarbon, a gas having a boiling point that is below room temperature (25° C.), or combinations of the above, that is condensed to a liquid phase and encapsulated. In one embodiment, the encapsulated droplets are activatable particles, such as phase change agents, or PCAs. The PCAs may be activated by exposure to ultrasonic, X-ray, optical, infrared, microwave, or radio frequency energy.

In one embodiment, the gas has a boiling point temperature in a range from approximately 50° C. to 40° C. at atmospheric pressure. In one embodiment, the gas has a boiling point temperature in a range from approximately 40° C. to 30° C. at atmospheric pressure. In one embodiment, the gas has a boiling point temperature in a range from approximately 30° C. to 20° C. at atmospheric pressure. In one embodiment, the gas has a boiling point temperature in a range from approximately 20° C. to 10° C. at atmospheric pressure. In one embodiment, the gas has a boiling point temperature in a range from approximately 10° C. to 0° C. at atmospheric pressure. In one embodiment, the gas has a boiling point temperature in a range from approximately 0° C. to 10° C. at atmospheric pressure. In one embodiment, the gas has a boiling point temperature in a range from approximately 10° C. to 20° C. at atmospheric pressure.

In one embodiment, encapsulating droplets of the liquid phase in the encapsulation material includes extruding or emulsifying the liquid phase using a microfluidics technique to produce droplets of the liquid phase and encapsulating the droplets of the liquid phase in the encapsulation material. In one embodiment, using a microfluidics technique comprises using a flow-focusing junction or a T-junction in a microfluidic device. In one embodiment, the device is maintained at a temperature below the phase transition temperature of the component having the lowest boiling point.

In one embodiment, at least some of the droplets range from approximately 10 um to 50 um in diameter. In one embodiment, at least some of the droplets range from approximately 5 um to 10 um in diameter. In one embodiment, at least some of the droplets range from approximately 1 um to 5 um in diameter. In one embodiment, at least some of the droplets range from approximately 800 nm to 1 um in diameter. In one embodiment, at least some of the droplets range from approximately 600 nm to 800 nm in diameter. In one embodiment, at least some of the droplets range from approximately 400 nm to 600 nm in diameter. In one embodiment, at least some of the droplets range from approximately 200 nm to 400 nm in diameter. In one embodiment, at least some of the droplets range from approximately 100 nm to 200 nm in diameter. In one embodiment, at least some of the droplets range from approximately 50 nm to 100 nm in diameter.

In one embodiment, the encapsulation material comprises a lipid, protein, polymer, gel, surfactant, peptide, or sugar. In one embodiment, the encapsulation material comprises lung surfactant proteins or their peptide components to form and stabilize bilayer and multilayer folds of the encapsulation material attached to maintain enough encapsulation material sufficient to fully encapsulate the liquid phase before droplet vaporization and the gas phase following vaporization. Example surfactants include amphiphilic polymers and copolymers, amphiphilic peptides, amphiphilic dendrimers, amphiphilic nucleic acids, and other amphiphiles.

In one experiment, this droplet extrusion method produced a highly varying size distribution of viable droplets, from droplets near the optical resolution of the test equipment (2~3 microns in diameter) to droplets more than 10 microns in diameter. The droplets so produced were stable at 37° C. and could be subsequently vaporized by ultrasonic energy Bubble Condensation Method.

Figure 3:
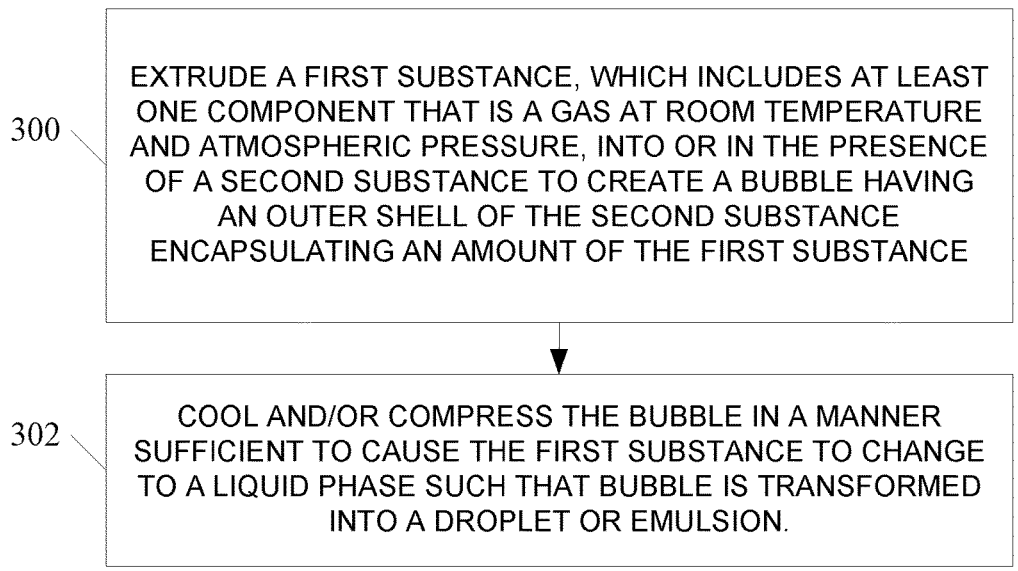

FIG. 3 is a flow chart illustrating an exemplary process for preparing particles of materials having a first substance that is enclosed by second substance that acts as an encapsulating material, where the first substance includes at least one component that is a gas at room temperature and atmospheric pressure, according to another embodiment of the subject matter described herein. At block 300, the first substance extruded into or in the presence of the second substance to create bubbles having an outer shell of the second substance encapsulating an amount of the first substance, at least some of which is in gaseous form. In one embodiment, the contents of the bubble are entirely or primarily in a gaseous phase. At block 302, the bubble thus formed is cooled and/or compressed such that the contents of the bubble reach a temperature below the phase transition temperature of the component having the lowest boiling point at that pressure. This causes the gas within the bubble to condense to a liquid phase, which transforms the bubble into a droplet or emulsion. In this manner, droplets or emulsions in which the first substance is encapsulated by the second substance are created. This method offers the advantage of making smaller, more uniform droplet sizes with peaks on the order of 200-300 nm—small enough for potential extravasation into solid tumors.

In one embodiment, the first substance includes a gas, such as a fluorocarbon, a perfluorocarbon, a chlorofluorocarbon, a hydrofluorocarbon, a hydrocarbon, a gas having a boiling point that is below room temperature (25° C.), or combinations of the above. In one embodiment, the encapsulated droplets are activatable particles, such as phase change agents, or PCAs. The PCAs may be activated by exposure to ultrasonic, X-ray, optical, infrared, microwave, or radio frequency energy.

In one embodiment, the gas has a boiling point temperature in a range from approximately 50° C. to 40° C. at atmospheric pressure. In one embodiment, the gas has a boiling point temperature in a range from approximately 40° C. to 30° C. at atmospheric pressure. In one embodiment, the gas has a boiling point temperature in a range from approximately 30° C. to 20° C. at atmospheric pressure. In one embodiment, the gas has a boiling point temperature in a range from approximately 20° C. to 10° C. at atmospheric pressure. In one embodiment, the gas has a boiling point temperature in a range from approximately 10° C. to 0° C. at atmospheric pressure. In one embodiment, the gas has a boiling point temperature in a range from approximately 0° C. to 10° C. at atmospheric pressure. In one embodiment, the gas has a boiling point temperature in a range from approximately 10° C. to 20° C. at atmospheric pressure.

In one embodiment, creating bubbles of a gas encapsulated in an encapsulation material includes extruding or emulsifying the gas in the presence of lipids. In one embodiment, creating bubbles of a gas encapsulated in an encapsulation material includes extruding or emulsifying the gas in a HEPES buffer. In one embodiment, creating bubbles of a gas encapsulated in an encapsulation material includes extruding or emulsifying the gas in a buffer having a pH in a range from approximately 3 to 9. In one embodiment, creating bubbles of a gas encapsulated in an encapsulation material includes extruding or emulsifying the gas in a buffer having a pH in a range from approximately 6 to 8.

In one embodiment, condensing the encapsulated gas into a liquid phase includes cooling the bubbles under pressure until the encapsulated gas condenses into a liquid phase. In one embodiment, the bubbles are cooled to a temperature in a range from approximately 0° C. to 10° C. In one embodiment, the bubbles are cooled to a temperature in a range from approximately 10° C. to 0° C. In one embodiment, the bubbles are cooled to a temperature in a range from approximately 20° C. to 10° C. In one embodiment, the bubbles are exposed to a pressure that is greater than 50 psi. In one embodiment, the bubbles are exposed to a pressure that is greater than 20 psi. In one embodiment, the bubbles are exposed to a pressure that is greater than 10 psi. In one embodiment, the bubbles are exposed to a pressure that is in a range from approximately 10 psi to 20 psi. In one embodiment, the bubbles are exposed to a pressure that is in a range from approximately 20 psi to 50 psi. In one embodiment, the bubbles are exposed to a pressure that is in a range from approximately 50 psi to 100 psi. In one embodiment, the bubbles are exposed to a pressure that is in a range from approximately 100 psi to 200 psi. In one embodiment, the bubbles are exposed to a pressure that is in a range from approximately 200 psi to 500 psi.

In one embodiment, at least some of the bubbles range from approximately 10 um to 50 um in diameter. In one embodiment, at least some of the bubbles range from approximately 5 um to 10 um in diameter. In one embodiment, at least some of the bubbles range from approximately 1 um to 5 um in diameter. In one embodiment, at least some of the droplets range from approximately 800 nm to 1 um in diameter. In one embodiment, at least some of the droplets range from approximately 600 nm to 800 nm in diameter. In one embodiment, at least some of the droplets range from approximately 400 nm to 600 nm in diameter. In one embodiment, at least some of the droplets range from approximately 200 nm to 400 nm in diameter. In one embodiment, at least some of the droplets range from approximately 100 nm to 200 nm in diameter. In one embodiment, at least some of the droplets range from approximately 50 nm to 100 nm in diameter.

In one embodiment, the encapsulation material includes a lipid, protein, polymer, gel, surfactant, peptide, or sugar. In one embodiment, the encapsulation material includes lung surfactant proteins or their peptide components to form and stabilize bilayer and multilayer folds of the encapsulation material attached to maintain enough encapsulation material sufficient to fully encapsulate the liquid phase before droplet vaporization and the gas phase following vaporization.

For both the droplet extrusion method and the bubble condensation method, the first substance may include a PFC that has a phase transition temperature that is below room temperature or below human body temperature of 37° C. at normal atmospheric pressure. For example, the first substance may include a highly volatile compound, such as DFP, OFP, a mixture of the two, or a mixture of DFP and/or OFP with another PFC. The first substance may also be a mixture of DFP and/or OFP with third substance, where the third substance may or may not be a gas at room temperature or body temperature. In one embodiment, the second substance may be made up of lipids, proteins, polymers, a gel, a surfactant, a peptide, a sugar, another suitable encapsulating material, or a combination of the above.

Whether the method of FIG. 2 or the method of FIG. 3 is used, the resulting droplets are stabile at room temperature/body temperature and pressure. Droplets containing DFB, OFP, or a combination have an activation energy that is low enough for use in human diagnostics, therapeutics, or treatment. For example, droplets containing DFP have the desired low vaporization threshold, even when prepared as sub-micron droplets. DFB's boiling point of −1.7° C. is significantly lower than other PFCs commonly used in ADV, which allows vaporization at much lower pressures than similarly-sized emulsions of higher boiling-point PFCs. Lipid-encapsulated nanodroplets containing condensed OFP, which has a boiling point of −40° C., are surprisingly stabile: exposing these nanodroplets to body temperature is not by itself enough to cause them to activate and expand into microbubbles; additional energy, such as may be provided by a medical ultrasound transceiver, is required. The resulting droplets are activatable with substantially less energy than other favored PCCA compounds. For example, when exposed in vitro to a 2 μs ultrasound pulse at 5 MHz and MI=1.2, the generated nanodroplets yield a distribution of microbubbles that corresponds well with expected expansion of the initial droplets through ideal gas law predictions with surface tension effects included.

The methods described in FIGS. 2 and 3 can be used to produce stabilized, lipid-encapsulated nanodroplets of highly volatile compounds suitable for use as extravascular ultrasound contrast agents and activatable using ADV at diagnostic ultrasound frequencies and mechanical indices within FDA guidelines for diagnostic imaging. The methods described above have routinely yielded droplets in the 200-300 nm range, which, upon activation, become bubbles between 1 and 5 microns in size. In other words, the droplets are small enough to extravasate, and, once activated, the bubbles are large enough to provide sufficient contrast for ultrasound imaging. As will be described in more detail below, the particles thus created are suitable for use in diagnostics, therapeutics, and treatment other than ultrasound imaging, such as drug and gene delivery.

It is noted, however, that the methods and techniques described herein may be used to create stable nanodroplets containing highly volatile PFCs, even those that have activation energies above the limits defined for human medical use. The unexpected stability of OFP droplets in the sub-micron range indicate that other highly volatile PFCs may be used to create nanodroplets that may be used to interrogate materials other than biological tissues, for example, to which a higher activation energy may be applied, e.g., where there is no concern about bioeffects.

Detailed Preparation.

In one embodiment, lipid films were prepared with a lipid composition containing 85 mole percent DPPC, 10 mole percent LPC, and 5 mole percent DPPE-PEG 2000. The lipids were dissolved in less than 1 mL of chloroform and gently evaporated with nitrogen gas. The lipids were kept under a lyophilzer overnight in order to remove residual solvent and to create lipid films. The lipid films were rehydrated with approximately 1 mL of HEPES buffer (pH=7.4) and sonicated for 10 minutes in a water bath sonicator at 50-60° C. The rehydrated films were subjected to 10 freeze-thaw cycles where the freezing section consisted of an isopropanol bath with dry ice and the thawing section was a 50-60° C. water bath. This created a homogeneous lipid suspension, which was also stirred for 10 minutes at 50-60° C. immediately afterwards. The resulting concentration of the lipid solution was about 20 mg/mL.

For the method described in FIG. 2, a PFC, such as DFB, was condensed in a container over dry ice. The condensed DFB was poured into a 2 mL glass vial and crimped. Two hundred microliters (200 μl) of DFB was then mixed with the lipid solution and the samples were extruded in a −20° C. cold room by 20 passes through a 1 μm porous membrane filter. After extrusion, the resulting emulsion was stored at 4° C. in a crimped 2 mL vial. Samples were observed throughout the extrusion process to make sure they did not freeze.

For the method described in FIG. 3, microbubbles of a PFC, such as DFB, were formulated by the dissolution DPPC, DPPE-PEG-2000, and TAPS in a molar ratio of 65:5:30 (mole:mole:mole) and a total lipid concentration of 0.75 mg/mL, 1.5 mg/mL, and 3 mg/mL. The excipient liquid was comprised of propylene glycol, glycerol, and normal saline. Microbubbles were formed via agitation by shaking for 45 seconds. The 2 mL vial containing the formed microbubbles was then immersed in a $CO_2$/isopropanol bath controlled to a temperature of approximately −5° C. A 25 G syringe needle containing 30 mL of room air was then inserted into the vial septum and the plunger depressed slowly. This step was repeated with another 30 mL of room air. Lipid freezing was avoided by observing the contents of the vial as well as the temperature of the $CO_2$/isopropanol solution periodically. After pressurizing with a total of 60 mL of room air, the syringe needle was removed from the vial, leaving a pressure head on the solution.

Analysis of Results.

The vaporization threshold of individual droplets was determined, and the size of the bubble resulting from activation of the droplet was measured. The vaporization threshold was determined by observing what level of ultrasound pressure was required to cause droplets of various diameters to activate. The measured pressure that induced vaporization was converted into a mechanical index (MI), defined as:

$$\frac{\text{Peak Negative Pressure (MPa)}}{\sqrt{\text{US Frequency (MHz)}}} \qquad (\text{Eq. \#10})$$

Figure 4:
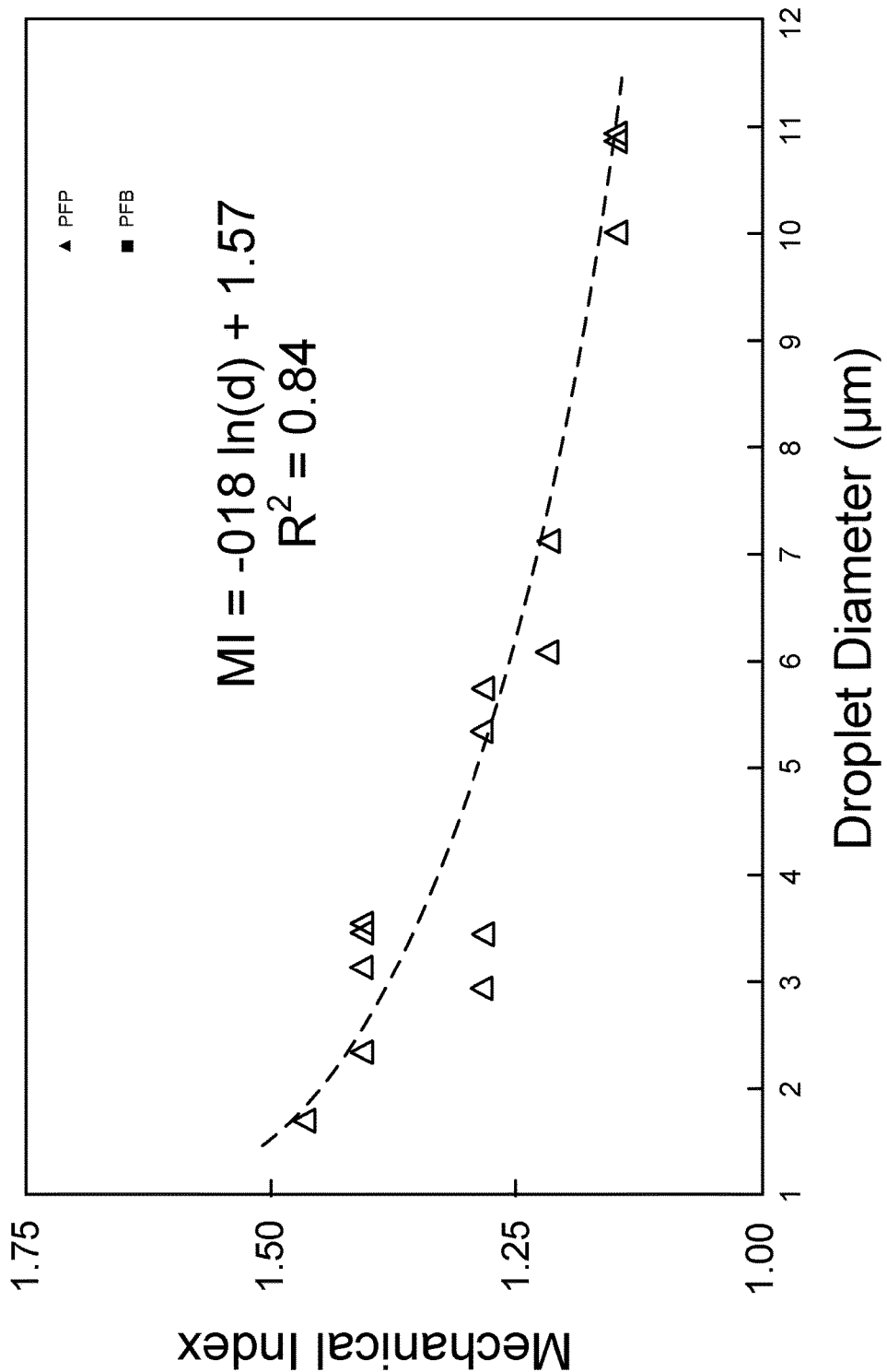

The results of the measurements are shown in FIG. 4.

FIG. 4 is a graph showing an observed relationship between initial diameter of a droplet and the mechanical index required to vaporize it. Droplets with diameters in the low micron range were seen to vaporize as an approximately logarithmic function of initial diameter. Droplets near the optical resolution limit of the experimental setup could be vaporized with brief 2 μs pulses at mechanical indices well-below the current clinical limit of 1.9 for diagnostic ultrasound imaging. Upon exposure to ultrasonic energy, vaporization of the largest content present in the samples— droplets larger than 1 μm, which could be resolved optically—was achieved at clinically relevant pressures such that a logarithmic relationship between initial diameter and pressure required to vaporize could be observed. As predicted, the pressure required to vaporize droplets was inversely related to droplet diameter.

Droplets produced by the droplet extrusion and bubble condensation methods were measured optically before and after activation, and it was observed that the resulting increase in volume after vaporization was close to that predicted by ideal gas laws (approximately 5 to 6 times the original droplet diameter).

Tunable activation energy.

Droplets generated according to the methods described herein have activation energies that depend on the size of the droplet and the substance encapsulated in the droplet. For example, droplets containing pure DFB, which has a boiling point of −1.7° C., has a higher activation energy than droplets containing pure OFP, which has a boiling point of −37.6° C. By creating droplets that contain a mixture of two substances each having a different boiling point, it is possible to create a droplet having a custom activation energy. This is shown in FIG. 5.

Figure 5:
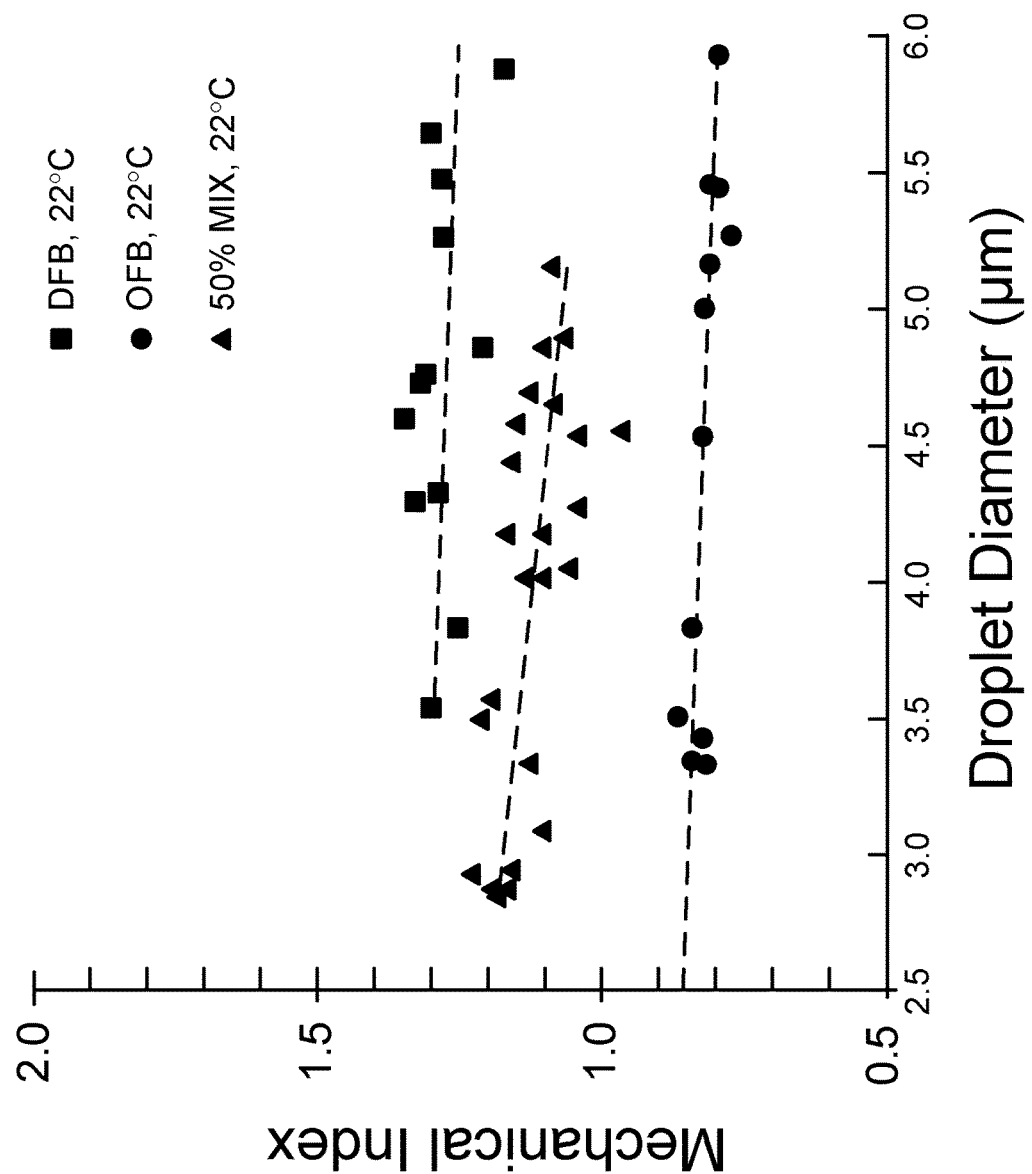

FIG. 5 is a graph showing mechanical index as a function of droplet diameter as observed using samples of droplets containing three different substances: DFB, OFP, and a 50%/50% mix of DFB and OFP, generated using the bubble condensation method according to an embodiment of the subject matter described herein. Due to the lower boiling point of OFP, a greater ambient pressure was needed before condensation of the sample was observed. In one embodiment, the DFP droplets produced had mean diameters of 360±156 nm (N=3). Also, due to the equipment used to verify the experimental results, only droplets larger than 1 micron were tested, but it is expected that sub-micron droplets would show analogous behavior. Droplets composed of a 50/50 mixture of DFB and OFP showed ultrasonic vaporization thresholds between that of each 'pure' perfluorocarbon at room temperature under the same test conditions.

It can be seen from the graph in FIG. 5 that droplets containing only DFB required a mechanical index of approximately 1.3 to activate, droplets containing only OFP required a mechanical index of approximately 0.8 to activate, and droplets containing the 50/50 mixture required a mechanical index in between 0.8 and 1.3, in the 1.1~1.2 range. By adjusting the mix of a relatively more volatile substance with a relatively less volatile substance, e.g., OFP and DFP, a droplet may be produced that has an activation energy that is somewhere in between the activation energies of the individual components of the mix. Thus, the energy required to vaporize a nanodroplet can be manipulated by simply mixing the gases to a desired ratio prior to condensation.

At both room and body temperature, DFB and OFP droplets were vaporized in vitro with waveforms similar to those found on clinical diagnostic ultrasound machines, and with pressures less than the current FDA limit at 8 MHz (approximately 5.4 MPa). Unexpectedly, OFP showed relative stability at room temperature (nearly 60° C. above its natural boiling point), but reacted highly upon exposure to body temperature. DFB droplets, on the other hand, showed remarkable stability at both room and body temperature. As expected, droplet stability correlated inversely with boiling point.

Applications.

FIG. 6 is a flow chart illustrating an exemplary process for delivery of particles to a target region according to an embodiment of the subject matter described herein. In the embodiment illustrated in FIG. 6, at block 600, particles comprising stable, activatable nanodroplets, each nanodroplet comprising a liquid encapsulated in a shell, wherein the liquid comprises at least one component that is a gas at room temperature and atmospheric pressure, are introduced into a blood vessel in the vicinity of a target region, and at 602, the method includes waiting until a sufficient amount of particles have extravasated into the target region. In one embodiment, the target region is exposed to some form of activation energy, such as ultrasonic, mechanical, thermal, or radio frequency energy, activating the nanodroplets and causing them to expand into microbubbles.

Figure 7:
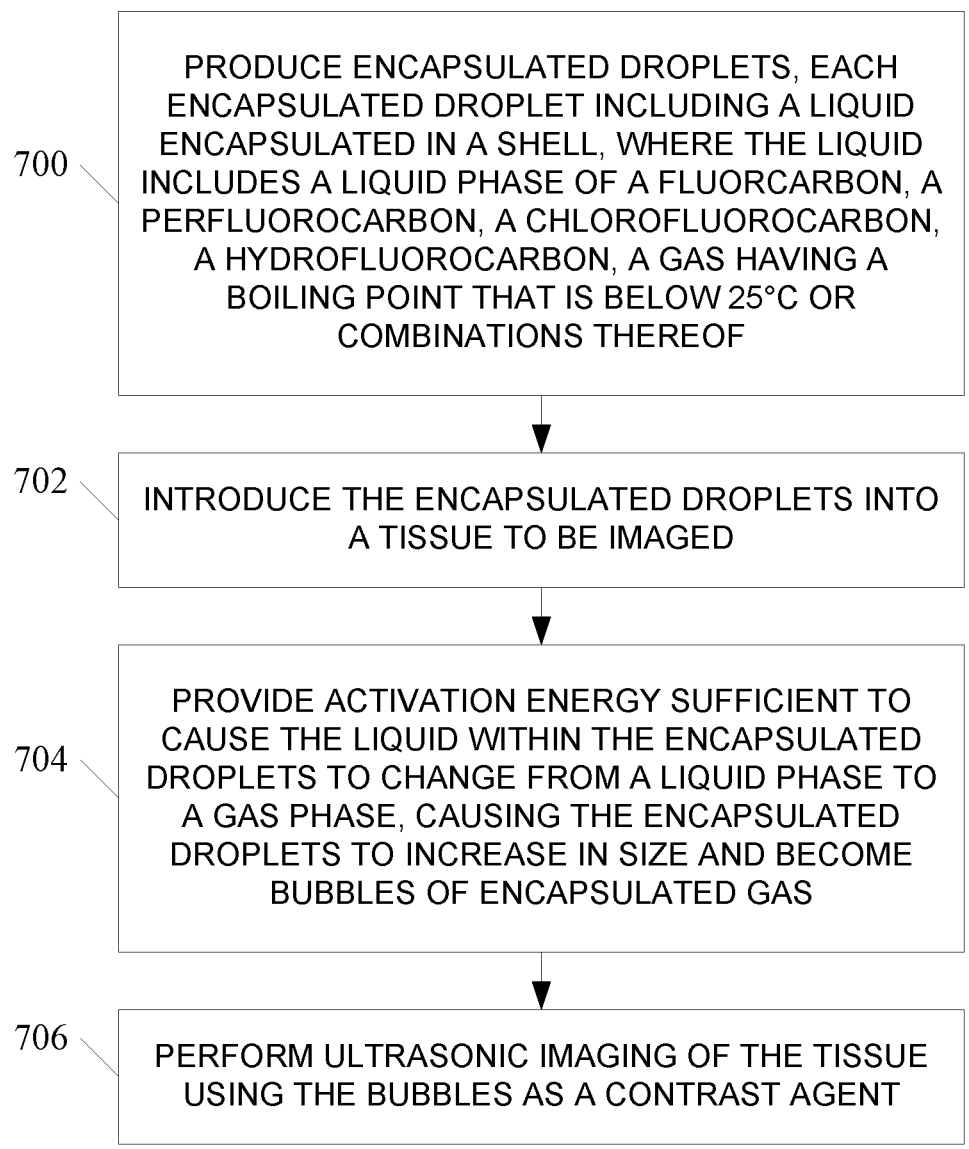

FIG. 7 is a flow chart illustrating an exemplary process for medical diagnostic imaging using activatable droplets as contrast agents according to an embodiment of the subject matter described herein. In the embodiment illustrated in FIG. 7, at block 700, encapsulated droplets, each encapsulated droplet comprising a liquid encapsulated in a shell, wherein the liquid comprises a liquid phase of a fluorocarbon, a perfluorocarbon, a chlorofluorocarbon, a hydrofluorocarbon, a hydrocarbon, a gas having a boiling point that is below room temperature (25° C.), or combinations thereof are produced. These droplets may be produced by using the droplet extrusion or bubble condensation methods described above, for example. At block 702, the encapsulated droplets so produced are introduced into a tissue to be imaged. In one embodiment, the droplets may be introduced into a blood vessel that is in proximity to the tissue to be imaged, which allows the droplets to extravasate into the interstitial area of the tissue. At block 704, activation energy sufficient to cause the liquid within the encapsulated droplets to change from a liquid phase to a gas phase is provided, causing the encapsulated droplets to increase in size and become bubbles of encapsulated gas. At block 706, ultrasonic imaging of the tissue is performed using the bubbles as a contrast agent.

In one embodiment, a method for medical diagnostic imaging using activatable droplets as contrast agents includes producing encapsulated droplets, each encapsulated droplet made up of a liquid encapsulated in a shell, where the liquid comprises a liquid phase of a fluorocarbon, a perfluorocarbon, a chlorofluorocarbon, a hydrofluorocarbon, a hydrocarbon, a gas having a boiling point that is below room temperature (25° C.), or combinations of the above. The encapsulated droplets are introduced into a tissue to be imaged, and activation energy sufficient to cause the liquid within the encapsulated droplets to change from a liquid phase to a gas phase is provided, causing the encapsulated droplets to increase in size and become bubbles of encapsulated gas. Ultrasonic imaging of the tissue using the bubbles as a contrast agent is performed. In one embodiment, the shell comprises a lipid, protein, polymer, gel, surfactant, peptide, or sugar. In one embodiment, the shell comprises lung surfactant proteins or their peptide components to form and stabilize bilayer and multilayer folds of the encapsulation material attached to maintain enough encapsulation material sufficient to fully encapsulate the liquid phase before droplet vaporization and the gas phase following vaporization. In one embodiment, providing activation energy sufficient to cause the liquid within the encapsulated droplets to change from a liquid phase to a gas phase includes subjecting the encapsulated droplets to ultrasonic, X-ray, optical, infrared, microwave, or radio frequency energy. In one embodiment, the encapsulating material contains a chemical substance that causes the encapsulated droplets to attach to cells of the tissue to be imaged. In one embodiment, the tissue to be imaged comprises cancerous or pre-cancerous cells and wherein the chemical substance attaches to proteins expressed by the cancerous or pre-cancerous cells.

This technology is amenable to not only ultrasound imaging, but drug and gene delivery and therapy as well. The low concentrations of lipids (0.75-3.0 mg/mL) utilized to stabilize the DFB droplets in one embodiment makes these formulations more amenable to human use while also minimizing the possibility of toxicity or bioeffects.

Figure 8:
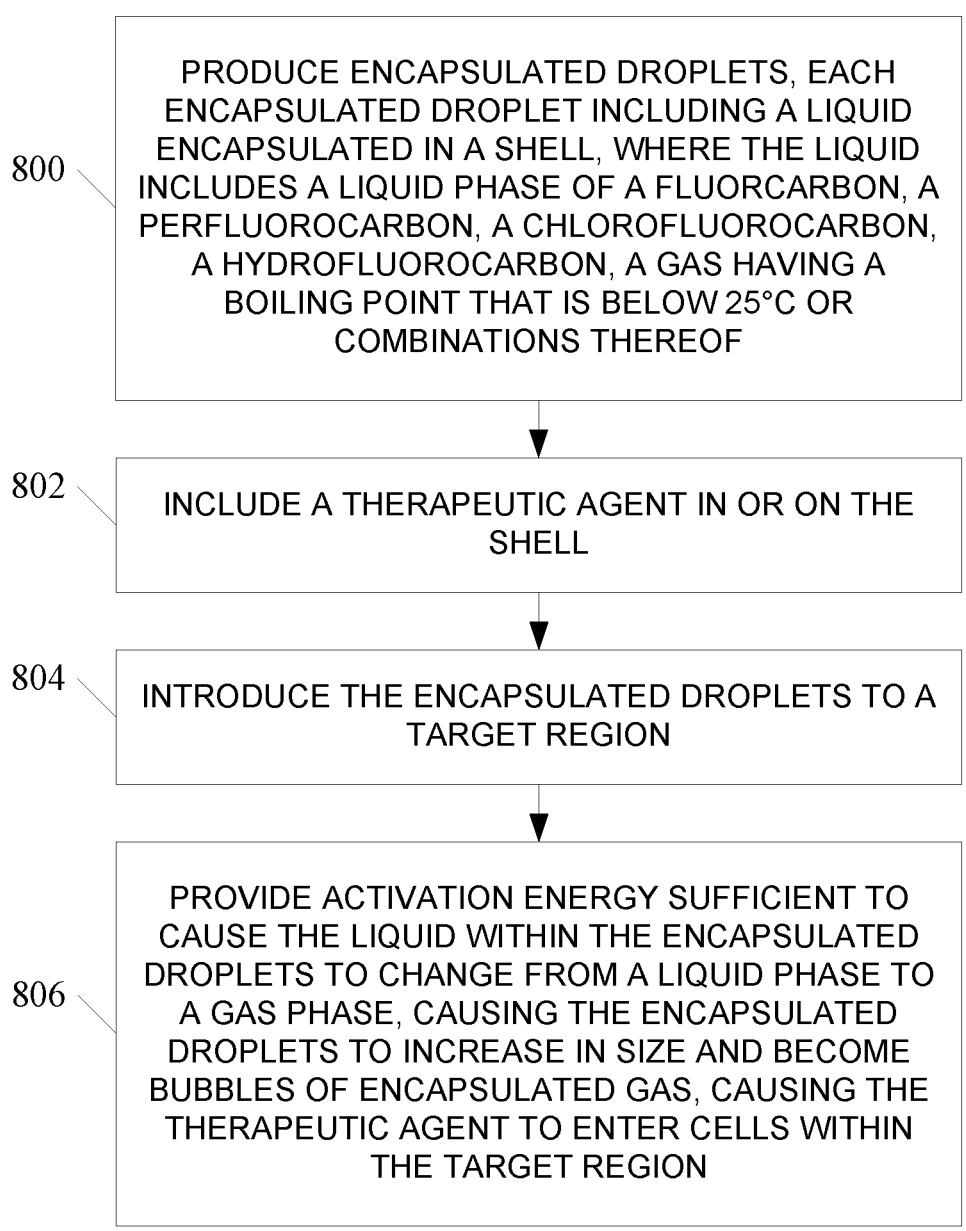

FIG. 8 is a flow chart illustrating an exemplary process for medical therapy using activatable droplets as a vehicle for delivering therapeutic agents according to an embodiment described herein. In the embodiment illustrated in FIG. 8, at block 800, encapsulated droplets, each encapsulated droplet comprising a liquid encapsulated in a shell, wherein the liquid comprises a liquid phase of a fluorocarbon, a perfluorocarbon, a chlorofluorocarbon, a hydrofluorocarbon, a hydrocarbon, a gas having a boiling point that is below room temperature (25° C.), or combinations thereof are produced. These droplets may be produced by using the droplet extrusion or bubble condensation methods described above, for example. At block 802, a therapeutic agent is included in or on the shell. In one embodiment, the droplets are produced first and the therapeutic agent is added into or onto the shell afterwards. In another embodiment, the therapeutic agent is included in the encapsulating material prior to encapsulation, such that therapeutic agent is present within the shell from the instant that the droplet is created. At block 804, the encapsulated droplets are delivered to a target region. At block 806, activation energy sufficient to cause the liquid within the encapsulated droplets to change from a liquid phase to a gas phase is provided, causing the encapsulated droplets to increase in size and become bubbles of encapsulated gas, and the therapeutic agent enters into one or more cells within the target region.

In one embodiment, a method for medical therapy using activatable droplets includes producing encapsulated droplets, each encapsulated droplet made up of a liquid encapsulated in a shell, where the liquid includes a liquid phase of a fluorocarbon, a perfluorocarbon, a chlorofluorocarbon, a hydrofluorocarbon, a hydrocarbon, a gas having a boiling point that is below room temperature (25° C.), or a combination of the above, and where a therapeutic agent is included in or on the shell. The encapsulated droplets are delivered to a target region, and activation energy sufficient to cause the liquid within the encapsulated droplets to change from a liquid phase to a gas phase is provided, causing the encapsulated droplets to increase in size and become bubbles of encapsulated gas, and where the substance to be delivered to the target tissue enters into the cells of the target tissue. In one embodiment, the shell comprises a lipid, protein, polymer, gel, surfactant, peptide, or sugar. In one embodiment, the shell comprises lung surfactant proteins or their peptide components to form and stabilize bilayer and multilayer folds of the encapsulation material attached to maintain enough encapsulation material sufficient to fully encapsulate the liquid phase before droplet vaporization and the gas phase following vaporization. In one embodiment, providing activation energy sufficient to cause the liquid within the encapsulated droplets to change from a liquid phase to a gas phase includes subjecting the encapsulated droplets to ultrasonic, X-ray, optical, infrared, microwave, or radio frequency energy. In one embodiment, the shell contains a chemical substance that causes the encapsulated droplets to attach to cells of the target tissue. In one embodiment, the shell contains a net negative or net positive charge to prevent aggregation and coalescence. In one embodiment, the shell contains a polymeric brush layer to prevent aggregation and coalescence. In one embodiment, the shell contains a chemical substance that causes plasmids or genes to attach to the shell. In one embodiment, the chemical substance is a cationic chemical. In one embodiment, the genes are targeted for gene or plasmid delivery to a cell.

In one embodiment, the target region comprises cancerous or pre-cancerous cells and wherein the chemical substance attaches to proteins expressed by the cancerous or pre-cancerous cells. In one embodiment, the encapsulated droplets are delivered to the target region by being introduced into a blood vessel in the vicinity of the target region and the encapsulated droplets extravasate into the target region. In one embodiment, the substance to be delivered to the target region enters into the cells of the target region via sonoporation, vaporization, endocytosis, or contact-facilitated diffusion. In one embodiment, the substance to be delivered to the target region includes a drug to be delivered to the target region and/or genetic material to be inserted into the cells of the target region.

In one embodiment, tissue-specific targeting ligands may be incorporated into the shell of nanodroplets. For example, tissue-specific targeting ligands may be incorporated into the shell of microbubbles produced and later condensed into nanodroplets according to the bubble condensation methods described above. In one embodiment, targeted DFB microbubbles were fabricated with DSPC, PEG, and PEG conjugated with a cyclic RGD peptide, which is known to target $\alpha_v\beta_3$, a known angiogenic biomarker. Likewise, control microbubbles were fabricated with DSPC, PEG and PEG conjugated with a cyclic RAD peptide, which does not bind to $\alpha_v\beta_3$. Targeted and non-targeted microbubbles were condensed into nanodroplets and incubated (15 minutes) independently with cover slips confluent with human umbilical vein endothelial cells (HUVEC), which overexpress $\alpha_v\beta_3$ integrin. After incubation, each cover slip was washed with cell media to remove any non-targeted droplets. Next, each cover slip was placed on a custom built holder and submerged in a water tank full of phosphate buffered saline heated to 37° C. for acoustic vaporization and testing. A linear array transducer was used to take 2D cross-sectional images across the cover slip as a baseline before vaporization. Then, the transducer was scanned at a constant speed of 2.5 mm/s across the cover slip at a mechanical index of 1.9 in power Doppler mode to vaporize any adherent droplets. Finally, 2D acquisitions across the cover slip were obtained with the transducer in contrast mode to determine the degree of contrast (via microbubbles from droplet vaporization) for both control and targeted samples. The brightness of adherent microbubbles was assumed to be correlated with the degree of $\alpha_v\beta_3$ expression. Analysis of ultrasound images shows that incorporating targeting ligands (in this case, the cyclic RGD peptide) increased the number of droplets present on the cell layer (HUVECs) dramatically. After being exposed to pressures within the limit of what a clinical ultrasound machine can provide, any droplets adhering to the cell layer were vaporized into microbubbles, which show up brightly on the ultrasound scan. Comparing targeted droplets to non-targeted droplets shows that the contrast present after vaporization was significantly greater for targeted droplets than for non-targeted droplets, indicating that 1) the targeting ligand was successfully preserved in the nanodroplet shell and 2) the targeted nanodroplets preferentially adhered to the cell layer. These results suggest successful 'transformation' of targeted microbubbles into targeted nanodroplets, which could be valuable for applications such as early detection and diagnosis of angiogenesis.

Delivering a droplet to targeted cells or to cells in a targeted region may involve more than simply delivering the substance to the exterior of the cell or into the vicinity of the cell. In one embodiment, the droplets may be coated with a material that causes the cells to internalize the droplets, such as via endocytosis or phagocytosis. For example, coating a droplet with folate may cause a cell to internalize the droplet. Once inside the cell, activation of the droplet causes the droplet to expand to microbubble size. In one embodiment, the activated droplet kills the cell, either by the expansion alone, or by subsequent excitation of the microbubble within the cell. Alternatively, the activated droplet may not kill the cell but instead deliver the intended payload more efficiently within the cell, e.g., by increasing the surface area of a shell containing a therapeutic substance intended for the cell to receive and use. In this manner, any substance that may be delivered into the presence of the cell (e.g., a drug to be delivered to the target region, genetic material to be inserted into the cells of the target region, and others) may instead be delivered into the interior of the cell directly.

In one embodiment, the droplet may be coated with a material that targets specific parts of the cell once internalized. For example, the droplet may be coated with a material that causes the droplet to attach itself, be internalized by, or otherwise target a subcellular organelle (e.g., mitochondria). In one embodiment, activating the droplet compromises the targeted organelle and subsequently destroying the cell, arresting the cell's growth, or otherwise killing the cell. In one embodiment, the droplet or its shell could contain a chemical substance which triggers cell apoptosis. Alternatively, the activated droplet may more efficiently deliver a chemical substance to the targeted organelle.

Figure 9:
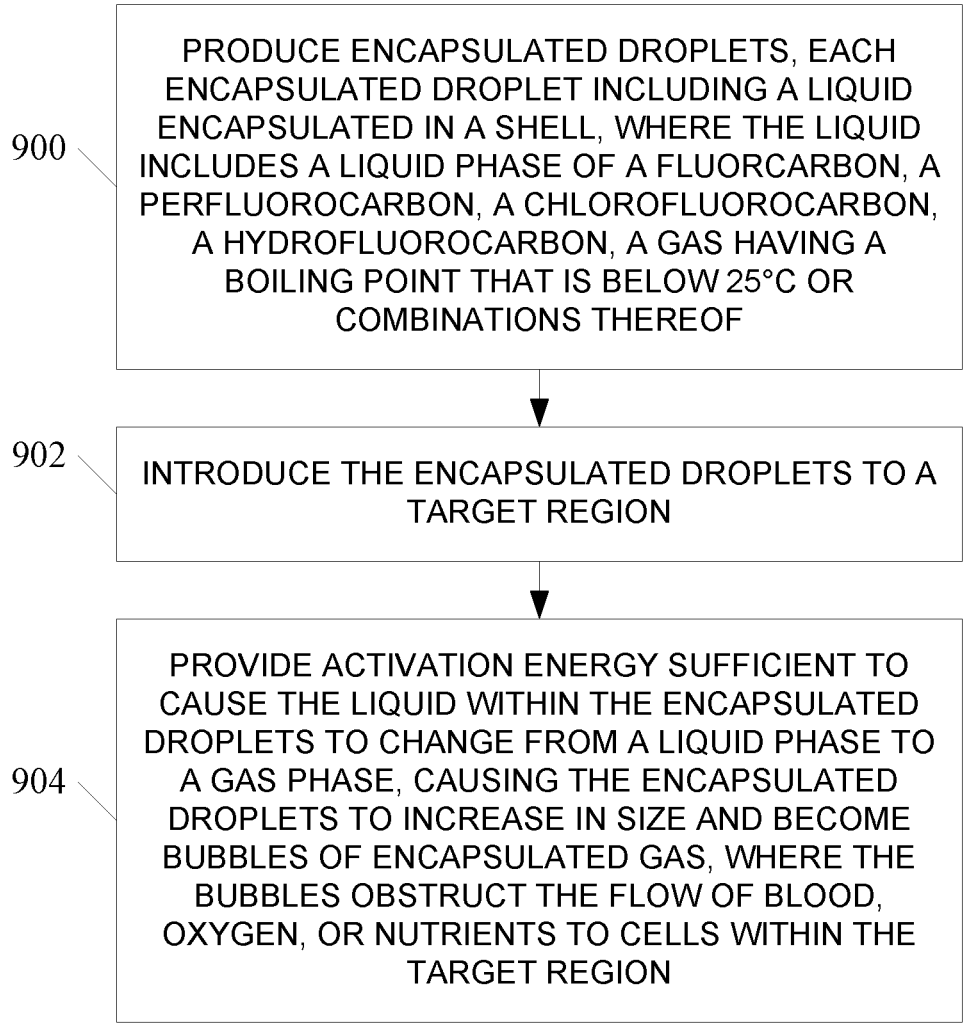

FIG. 9 is a flow chart illustrating an exemplary process for medical therapy using activatable droplets to obstruct the flow of blood, oxygen, or nutrients to cells, such as tumor tissues, according to an embodiment of the subject matter described herein. In the embodiment illustrated in FIG. 9, at block 900, encapsulated droplets, each encapsulated droplet comprising a liquid encapsulated in a shell, wherein the liquid comprises a liquid phase of a fluorocarbon, a perfluorocarbon, a chlorofluorocarbon, a hydrofluorocarbon, a hydrocarbon, a gas having a boiling point that is below room temperature (25° C.), or combinations thereof are produced. These droplets may be produced by using the droplet extrusion or bubble condensation methods described above, for example. At block 902, the encapsulated droplets are delivered to a target region. At block 904, activation energy sufficient to cause the liquid within the encapsulated droplets to change from a liquid phase to a gas phase is provided, causing the encapsulated droplets to increase in size and become bubbles of encapsulated gas, and the bubbles obstruct the flow of blood, oxygen, or nutrients to cells within the target region. In one embodiment, the droplets are small enough to extravasate into the interstitial space of tissues in the target region, and the activated bubbles prevent nutrients from passing to the tissue from blood vessels. In one embodiment, the droplets remain within the blood vessels and, when activated, are large enough to obstruct blood flow through the blood vessels, which also may starve tissue within the target region. Example target regions may include tumors, cancerous cells, or pre-cancerous cells.

Figure 10:
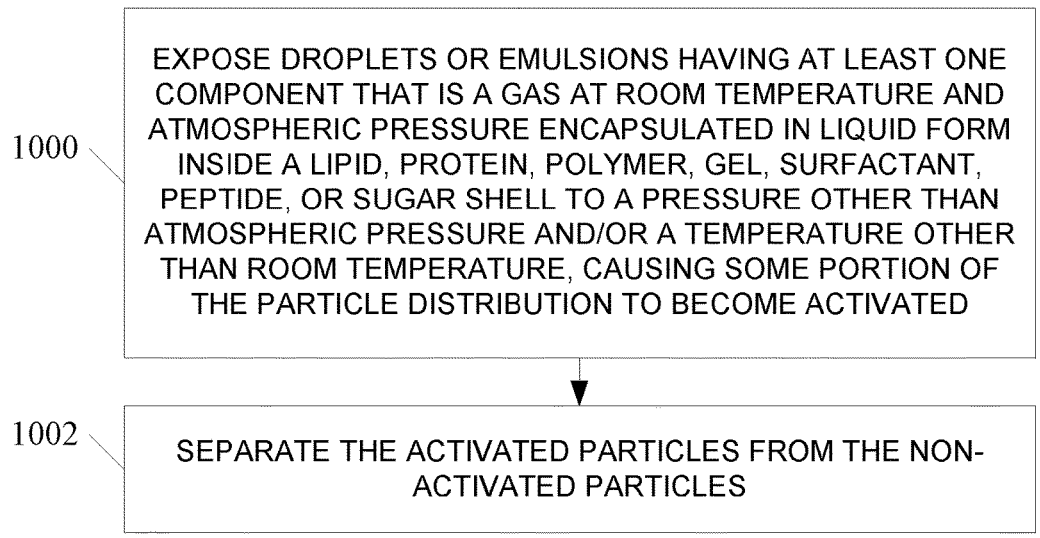

FIG. 10 is a flow chart illustrating an exemplary process for size selection of particles according to an embodiment described herein. In the embodiment illustrated in FIG. 10, at block 1000, droplets or emulsions having at least one component that is a gas at room temperature and atmospheric pressure encapsulated in liquid form inside a lipid, protein, or polymer capsule particles are exposed to a pressure other than atmospheric pressure and/or a temperature other than room temperature, which causes some portion of the particle distribution to become activated. At block 1002, the activated particles can then be separated from the non-activated particles. This is fairly easy to do since bubbles are more buoyant than droplets. This technique allows the particles to be selectively separated according to droplet size. The larger droplets have a lower activation energy than the smaller droplets, and so the larger droplets may be separated from the other droplets by applying an activation energy that is high enough to activate the larger droplets but not high enough to activate the smaller droplets. If smaller droplets are desired, this technique can be used to cull larger droplets from the mix. If larger droplets are desired, the technique can be used to harvest the larger droplets by causing them to inflate into bubbles, scooping the now floating bubbles from the top, and subject them to cooling and/or compression to cause them to revert to droplet form.

In one embodiment, a method of size selection of particles comprising droplets or emulsions having at least one component that is a gas at room temperature and atmospheric pressure encapsulated in liquid form inside a lipid, protein, polymer, gel, surfactant, peptide, or sugar capsule includes exposing the particles to pressure other than atmospheric pressure thereby causing some portion of the particle distribution to become activated, and separating the activated particles from the non-activated particles. In one embodiment, exposing the particles to pressure other than atmospheric pressure includes exposing the particles to a pressure that is 0~10 mm Hg below atmospheric pressure. In one embodiment, exposing the particles to pressure other than atmospheric pressure includes exposing the particles to a pressure that is 10~50 mm Hg below atmospheric pressure. In one embodiment, exposing the particles to pressure other than atmospheric pressure includes exposing the particles to a pressure that is 50~100 mm Hg below atmospheric pressure. In one embodiment, exposing the particles to pressure other than atmospheric pressure includes exposing the particles to a pressure that is 100~200 mm Hg below atmospheric pressure. In one embodiment, exposing the particles to pressure other than atmospheric pressure includes exposing the particles to a pressure that is 200~400 mm Hg below atmospheric pressure. In one embodiment, exposing the particles to pressure other than atmospheric pressure includes exposing the particles to a pressure that is 400~600 mm Hg below atmospheric pressure. In one embodiment, exposing the particles to pressure other than atmospheric pressure includes exposing the particles to a pressure that is 600~800 mm Hg below atmospheric pressure.

In one embodiment, a method of size selection of particles comprising droplets or emulsions having at least one component that is a gas at room temperature and atmospheric pressure encapsulated in liquid form inside a lipid, protein, polymer, gel, surfactant, peptide, or sugar capsule includes exposing the particles to a temperature range thereby causing some portion of the particle distribution to become activated, and separating the activated particles from the non-activated particles. In one embodiment, exposing the particles to a temperature range includes exposing the particles to a temperature that is 0~60 degrees C. above room temperature. In one embodiment, exposing the particles to a temperature range includes exposing the particles to a temperature that is 10~60 degrees C. above room temperature. In one embodiment, exposing the particles to a temperature range includes exposing the particles to a temperature that is 20~80 degrees C. above room temperature.

In one embodiment, a method of generating microbubbles in a biological media using a metastable nanoparticle containing a stabilized fluorocarbon with a boiling point below the temperature of the biological media and activating the nanoparticle, causing the nanoparticle to transform into a microbubble. In one embodiment, the boiling point is between 0 and 60 degrees C. below the temperature of the biological media. In one embodiment, the boiling point is between 10 and 60 degrees C. below the temperature of the biological media. In one embodiment, the boiling point is between 20 and 80 degrees C. below the temperature of the biological media. In one embodiment, the boiling point is between 30 and 80 degrees C. below the temperature of the biological media. In one embodiment, the boiling point is between 40 and 60 degrees C. below the temperature of the biological media. In one embodiment, the boiling point is between 50 and 60 degrees C. below the temperature of the biological media.

In one embodiment, a method for medical therapy using activatable droplets includes producing encapsulated droplets, each encapsulated droplet made up of a liquid encapsulated in a shell, where the liquid includes a liquid phase of a fluorocarbon, a perfluorocarbon, a chlorofluorocarbon, a hydrofluorocarbon, a hydrocarbon, a gas having a boiling point that is below room temperature (25° C.), or combinations of the above. The encapsulated droplets are delivered to a target tissue, and activation energy sufficient to cause the liquid within the encapsulated droplets to change from a liquid phase to a gas phase is provided, causing the encapsulated droplets to increase in size and become bubbles of encapsulated gas. The bubbles so generated obstruct the flow of blood, oxygen, or nutrients to a target region. In one embodiment, the shell includes a lipid, protein, polymer, gel, surfactant, peptide, or sugar. In one embodiment, the shell includes lung surfactant proteins or their peptide components to form and stabilize bilayer and multilayer folds of the encapsulation material attached to maintain enough encapsulation material sufficient to fully encapsulate the liquid phase before droplet vaporization and the gas phase following vaporization. In one embodiment, providing activation energy sufficient to cause the liquid within the encapsulated droplets to change from a liquid phase to a gas phase includes subjecting the encapsulated droplets to ultrasonic, X-ray, optical, infrared, microwave, or radio frequency energy. In one embodiment, the target region includes a tumor, cancerous cells, or pre-cancerous cells. In one embodiment, the encapsulating material contains a chemical substance that causes the encapsulated droplets to attach to cells of a tissue within the cells of the target region. In one embodiment, the encapsulating material contains a chemical substance that causes the encapsulated droplets to attach to cells and promote intracellular uptake. In one embodiment, the chemical substance attaches to proteins expressed by cells within the target region.

CONCLUSION

It has been shown that highly volatile PFCs, such as DFB and OFP, can be successfully generated as lipid-encapsulated micron and sub-micron sized droplets that remain stable at physiological temperatures. Most studies of phase-change contrast agents to date have chosen PFCs that are stable at room temperature, presumably due to simplicity of droplet generation. This study is the first, to the knowledge of the authors, which has explored the use of lower boiling-point PFCs by means of using shell encapsulation to produce stable liquid droplets of PFCs which are normally gas at room and body temperature. DFB-based phase-change contrast agents show significant potential for applications such as intra-tumoral deposition of chemotherapeutics and the imaging of interstitial space.

It has also been shown that pressurization and temperature-induced condensation of pre-formed microbubbles is both an effective and advantageous means of producing contrast agents for ADV applications compared to conventional extrusion and emulsion-based methods for some PFCs. The samples formed at a lipid concentration of 3 mg/mL produced a high number of viable nanodroplets that could be vaporized at clinically feasible pressures, resulting in a distribution of contrast-providing microbubbles well-correlated to the original microbubble sample. This method also may have advantages with regard to commercialization of ADV technology, as nanodroplets can be formed easily by adding a simple technique after traditional microbubble preparation. Results have demonstrated that ADV of sub-micron sized droplets can be induced in vitro with pressures available to clinical diagnostic ultrasound machines.

What is claimed is:

1. A method of producing particles of materials for ultrasound activation, comprising:
    condensing, from a gaseous phase to a liquid phase, a first substance comprising at least one component that is a perfluorocarbon or perfluorochemical having a boiling point below 25° C. at atmospheric pressure;
    extruding or emulsifying the first substance into or in the presence of a second substance to create a droplet having a diameter of less than one micron and in which the first substance is encapsulated by the second substance and wherein at least some of the first substance exists in the liquid phase at the time of encapsulation of the first substance within the second substance, and wherein the droplet is an activatable phase change agent that remains a droplet having a core that will remain in the liquid phase at a boiling point of the first substance and atmospheric pressure.

2. The method of claim 1 wherein the first substance comprises at least one of decafluorobutane (DFB) or octafluoropropane (OFP).

3. The method of claim 1 wherein causing the first substance to condense to a liquid phase comprises cooling the first substance.

4. The method of claim 3 wherein causing the first substance to condense to a liquid phase comprises cooling the first substance to a temperature that is below the liquid-to-gas phase transition temperature of a component of the first substance having the lowest liquid-to-gas phase transition temperature.

5. The method of claim 1 wherein causing the first substance to condense to a liquid phase comprises compressing the first substance.

6. The method of claim 5 wherein causing the first substance to condense to a liquid phase comprises compressing the first substance to a pressure that is above the gas-to-liquid phase transition pressure of a component of the first substance having the highest gas-to-liquid phase transition pressure.

7. The method of claim 1 wherein the second substance comprises at least one of a lipid, a protein, a polymer, a gel, a surfactant, a peptide, or a sugar.

8. The method of claim 1 wherein the second substance comprises lung surfactants, amphiphiles, proteins, or peptide components thereof in a sufficient quantity to fully encapsulate the liquid phase of the first substance.

9. The method of claim 1 wherein the amphiphiles comprise at least one of amphiphilic polymers and copolymers, amphiphilic peptides, amphiphilic dendrimers, or amphiphilic nucleic acids.

10. The method of claim 1 wherein the first substance consists of a single perfluorocarbon or perfluorochemical having a single activation energy.

11. The method of claim 1 wherein extruding or emulsifying the first substance into or in the presence of a second substance includes extruding the first substance through a filter.

12. The method of claim 11 wherein the filter has a pore size greater than a desired particle size.

13. The method of claim 1 wherein extruding or emulsifying the first substance into or in the presence of a second substance includes using a microfluidics technique to produce the droplet in which the first substance is encapsulated within the second substance.

14. The method of claim 13 wherein using the microfluidics technique includes using a flow focusing or T junction in a microfluidics device to produce the droplet in which the first substance is encapsulated within the second substance.

* * * * *